(12) United States Patent
Meisinger et al.

(10) Patent No.: US 10,718,784 B2
(45) Date of Patent: Jul. 21, 2020

(54) MITOCHONDRIAL PREPROTEINS AS MARKERS FOR ALZHEIMER'S DISEASE

(71) Applicant: Albert-Ludwigs-Universität Freiburg, Freiburg (DE)

(72) Inventors: Chris Meisinger, Freiburg (DE); Nora Vögtle, Freiburg (DE); Dirk Mossmann, Freiburg (DE); Elzbieta Glaser, Täby (SE); Caroline Graff, Sollentuna (SE); René P. Zahedi, Dortmund (DE)

(73) Assignee: Albert-Ludwigs-Universität Freiburg, Freiburg (DE)

( * ) Notice: Subject to any disclaimer, the term of this patent is extended or adjusted under 35 U.S.C. 154(b) by 0 days.

(21) Appl. No.: 15/124,216

(22) PCT Filed: Mar. 6, 2015

(86) PCT No.: PCT/EP2015/054757
§ 371 (c)(1),
(2) Date: Sep. 7, 2016

(87) PCT Pub. No.: WO2015/132397
PCT Pub. Date: Sep. 11, 2015

(65) Prior Publication Data
US 2017/0108513 A1 Apr. 20, 2017

(30) Foreign Application Priority Data

Mar. 7, 2014 (EP) .................................... 14158408

(51) Int. Cl.
*G01N 33/68* (2006.01)
*G01N 33/50* (2006.01)

(52) U.S. Cl.
CPC ..... *G01N 33/6896* (2013.01); *G01N 33/6842* (2013.01); *C12Y 101/01037* (2013.01); *G01N 33/5079* (2013.01); *G01N 33/6848* (2013.01); *G01N 2500/04* (2013.01); *G01N 2800/2821* (2013.01)

(58) Field of Classification Search
CPC ........... G01N 33/6842; G01N 33/6848; G01N 33/53; G01N 33/5076; G01N 33/5079; G01N 33/6896; G01N 2800/2821; C12Y 101/01037; C12Y 304/24064
See application file for complete search history.

(56) References Cited

U.S. PATENT DOCUMENTS

2004/0101874 A1* 5/2004 Ghosh ................ G01N 33/5079 435/6.12
2011/0229912 A1* 9/2011 Cai ......................... C07K 16/18 435/7.9

FOREIGN PATENT DOCUMENTS

WO WO-00/55350 A1 9/2000
WO WO-03/087768 A2 10/2003
WO WO-2015/132397 A2 9/2015

OTHER PUBLICATIONS

Bubber P et al. Mitochondrial abnormalities in Alzheimer brain: Mechanistic implications. Ann. Neurol. 2005, 57:695-703.*
Mossnnann D et al. Processing of mitochondrial presequences. Biochim et Biophys Acta, 1819, 1098-1106. (Year: 2012).*
Omura T. Mitochondria-targeting sequence, a multi-role sorting sequence recognized at all steps of protein import into mitochondria . J. Biochem. 123, 1010-1016. (Year: 1998).*
Chen X et al. Mammalian mitochondrial proteomics: insights into mitochondrial functions and mitochondria-related diseases. Expert Reviews Proteomics, 7(3):333-345. (Year: 2010).*
Morais VA and De Strooper B. Mitochondria dysfunction and neurodegenerative disorders: Cause or consequence. J. Alzheimer's Disease, 20:S255-S263. (Year: 2010).*
Mossmann D et al. Processing of mitochondrial presequences. Biochimica et Biophysica Acta, 1819:1098-1106. (Year: 2012).*
Pfanner N. Protein sorting: Recognizing mitochondrial presequences. Current Biology, 10:R412-R415. (Year: 2000).*
Roise D and Schatz G. Mitochondrial presequences. J. Biol. Chem. 263(10):4509-4511. (Year: 1988).*
Alam et al. (2012) Flow cytometric lymphocyte subset analysis using material from frozen whole blood. Journal of immunoassay & immunochemistry 33(2):128-139.
Burkhart et al. (2011) Quality control of nano-LC-MS systems using stable isotope-coded peptides. Proteomics 11:1049-1057.
Crouch et al. (2008) Mechanisms of Aβ mediated neurodegeneration in Alzheimer's disease. Int. J. Biochem. Cell Biol. 40:181-198.
Dolezal et al. (2006) Evolution of the molecular machines for protein import into mitochondria. Science 313:314-318.
Gevaert et al. (2003) Exploring proteomes and analyzing protein processing by mass spectrometric identification of sorted N-terminal peptides. Nat. Biotechnol. 21:566-569.
Hardy et al. (2002) The amyloid hypothesis of Alzheimer's disease: progress and problems on the road to therapeutics. Science 297:353-356.
Hawlitschek et al. (1998) Mitochondrial protein import: identification of processing peptidase and of PEP, a processing enhancing protein. Cell 53:795-806.
Ittner et al. (2011) Amyloid-β and tau—a toxic pas de deux in Alzheimer's disease. Nat. Rev. Neurosci. 12:65-72.
Larsson (2010) Somatic mitochondrial DNA mutations in mammalian aging. Ann. Rev. Biochem. 79:683-706.
Lustbader et al. (2004) ABAD directly links Abeta to mitochondrial toxicity in Alzheimer's disease. Science 304:448-452.

(Continued)

*Primary Examiner* — Kimberly Ballard
(74) *Attorney, Agent, or Firm* — Jenkins, Wilson, Taylor & Hunt, P.A.

(57) ABSTRACT

The present invention is inter alia concerned with a method of diagnosing Alzheimer's disease in a patient, wherein said method is based on determining the amount of at least one premature mitochondrial protein. Further, the present invention relates to the use of such a protein as marker for Alzheimer's disease. Accordingly, antibodies binding to such a preprotein may be used for diagnosing Alzheimer's disease. The present invention is based on the finding that premature mitochondrial proteins accumulate in Alzheimer's disease.

3 Claims, 9 Drawing Sheets

Specification includes a Sequence Listing.

(56) References Cited

OTHER PUBLICATIONS

Ozmen et al. (2009) Expression of transgenic APP mRNA is the key determinant for beta-amyloid deposition in PS2APP transgenic mice. Neurodegener. Dis. 6:29-36.
Staes et al. (2011) Selecting protein N-terminal peptides by combined fractional diagonal chromatography. Nat. Protoc. 6:1130-1141.
Stojanovski et al. (2007) Import of proteins into mitochondria. Meth. Cell Biol. 80:783-806.
Alikhani et al., Decreased proteolytic activity of the mitochondrial amyloid-β degrading enzyme, PreP peptidasome, in Alzheimer's disease brain mitochondria. J. Alzheimers Dis. 27, 75-87 (2011).
Area-Gomez et al., Upregulated function of mitochondria-associated ER membranes in Alzheimer disease. EMBO J. 31, 4106-4123 (2012).
Begcevic et al., Semiquantitative proteomics analysis of human hippocampal tissues from Alzheimer's disease and age-matched control brains. Clinical Proteomics 10, 5 (2013).
Caine et al., Alzheimer's Abeta fused to green fluorescent protein induces growth stress and a heat shock response. FEMS Yeast Res. 7, 1230-1236 (2007).
Du et al., Cyclophilin D deficiency attenuates mitochondrial and neuronal perturbation and ameliorates learning and memory in Alzheimer's disease. Nat. Med. 14, 1097-1105 (2008).
Falkevall et al., Degradation of the amyloid β-protein by the novel mitochondrial peptidasome, PreP. J. Biol. Chem. 281, 29096-29104 (2006).
Géli, Functional reconstitution in *Escherichia coli* of the yeast mitochondrial matrix peptidase from its two inactive subunits. Proc. Natl. Acad. Sci. USA. 90, 6247-6251 (1993).
Hansson Petersen et al., The amyloid β-peptide is imported into mitochondria via the TOM import machinery and localized to mitochondrial cristae. Proc. Natl. Acad. Sci. USA. 105, 13145-13150 (2008).
International Preliminary Report on Patentability corresponding to European patent application No. PCT/EP2015-054757 dated Sep. 13, 2016.
International Search Report corresponding to European patent application No. PCT/EP2015-054757 dated Oct. 16, 2015.
Kambacheld et al., Role of the novel metallopeptidase MoP112 and Saccharolysin for the complete degradation of proteins residing in different subcompartments of mitochondria. J. Biol. Chem. 280, 20132-20139 (2005).
Kondo-Okamoto et al., Mmm1p spans both the outer and inner mitochondrial membranes and contains distinct domains for targeting and foci formation. J. Biol. Chem. 278, 48997-49005 (2003).
Kushnirov, Rapid and reliable protein extraction from yeast. Yeast 16, 857-860 (2000).
Longtine et al., Additional modules for versatile and economical PCR-based gene deletion and modification in *Saccharomyces cerevisiae*. Yeast 14, 953-961 (1998).
Manczak et al., Mitochondria are a direct site of Aβ accumulation in Alzheimer's disease neurons: implications for free radical generation and oxidative damage in disease progression. Hum. Mol. Genet. 15, 1437-1449 (2006).
Morais et al., Mitochondria dysfunction and neurodegenerative disorders: cause or consequence. J. Alzheimers Dis. 20, 255-263(2010).
Mukhopadhyay et al., Precursor protein is readily degraded in mitochondrial matrix space if the leader is not processed by mitochondrial processing peptidase. J. Biol. Chem. 282, 37266-37275 (2007).
Rhein et al., Amyloid-β and tau synergistically impair the oxidative phosphorylation system in triple transgenic Alzheimer's disease mice. Proc. Natl. Acad. Sci. USA 106, 20057-20062 (2009).
Selfridge et al., Role of mitochondrial homeostasis and dynamics in Alzheimer's disease. Neurobiol. Dis. 51, 3-12 (2013).
Sikorski et al., A system of shuttle vectors and yeast host strains designed for efficient manipulation of DNA in *Saccharomyces cerevisiae*. Genetics 122, 19-27 (1989).
Stahl et al., Isolation and identification of a novel mitochondrial metalloprotease (PreP) that degrades targeting presequences in plants. J. Biol. Chem. 277, 41931-41939 (2002).
Tardiff et al., Yeast reveal a "druggable" Rsp5/Nedd4 network that ameliorates β-synuclein toxicity in neurons. Science 342, 979-983 (2013).
Treusch et al., Functional links between Aβ toxicity, endocytic trafficking, and Alzheimer's disease risk factors in yeast. Science 334, 1241-1245 (2011).
Varshavsky, The N-end rule pathway and regulation by proteolysis. Protein Sci. 20, 1298-1345 (2011).
Vögtle et al., Global analysis of the mitochondrial N-proteome identifies a processing peptidase critical for protein stability. Cell 139, 428-439 (2009).
Vögtle et al., Intermembrane space proteome of yeast mitochondria. Mol. Cell Proteomics 11, 1840-1852 (2012).
Vögtle et al., Mitochondrial protein turnover: role of the precursor intermediate peptidase Oct1 in protein stabilization. Mol. Biol. Cell 22, 2135-2143 (2011).
Walls et al., Swedish Alzheimer mutation induces mitochondrial dysfunction mediated by HSP60 mislocalization of amyloid precursor protein (APP) and beta-amyloid. J. Biol. Chem. 287, 30317-30327 (2012).
Witte et al., MAS1, a gene essential for yeast mitochondrial assembly, encodes a subunit of the mitochondrial processing protease. EMBO J. 7, 1439-1447 (1988).
Yang et al., The MAS-encoded processing protease of yeast mitochondria. Interaction of the purified enzyme with signal peptides and a purified precursor protein. J. Biol. Chem. 266, 6416-6423 (1991).
Yao et al., Mitochondrial bioenergetic deficit precedes Alzheimer's pathology in female mouse model of Alzheimer's disease. Proc. Natl. Acad. Sci. USA 106, 14670-14675 (2009).

\* cited by examiner

MITOCHONDRIAL PREPROTEINS AS MARKERS FOR ALZHEIMER'S DISEASE

FIELD OF THE INVENTION

The present invention relates to a method of diagnosing Alzheimer's disease in a patient. The present invention further relates to the use of at least one premature mitochondrial protein as marker for Alzheimer's disease and the use of an antibody directed against a mitochondrial protein for diagnosing Alzheimer's disease. The present invention further discloses specific antibodies and is also concerned with an anti-inflammatory agent and/or antioxidant for use in treating Alzheimer's disease in a specific patient population and methods of screening for a compound effective against Alzheimer's disease.

BACKGROUND OF THE INVENTION

Alzheimer's disease (AD) is the most common form of dementia. Most often, AD is diagnosed in people over 65 years of age, although the less prevalent early-onset AD can occur much earlier. AD worsens as it progresses and eventually leads to death. To date there is no cure for the disease. AD develops for an unknown and variable amount of time before becoming fully apparent, and it can progress undiagnosed for years.

AD is characterized by loss of neurons and synapses in the cerebral cortex and certain subcortical regions. This loss results in gross atrophy of the affected regions, including degeneration in the temporal lobe and parietal lobe, and parts of the frontal cortex and cingulate gyrus. Studies using MRI and PET have documented reductions in the size of specific brain regions in people with AD as they progressed from mild cognitive impairment to AD and in comparison with similar images from healthy older adults.

AD is usually diagnosed clinically from the patient history, collateral history from relatives, and clinical observations, based on the presence of characteristic neurological and neuropsychological features and the absence of alternative conditions. Advanced medical imaging with CT or MRI and SPECT or PET can be used to help exclude other cerebral pathology. Assessment of intellectual functioning including memory testing can further characterize the state of the disease. The diagnosis can be confirmed with very high accuracy post-mortem when brain material is available and can be examined histologically.

As can be derived from the above introductory statements taken from wikipedia (en.wikipedia.org), there is currently no reliable method of diagnosing AD in a living subject potentially suffering from the disease using a marker, i.e. an in vitro test, let alone of diagnosing an early stage of the disease using a marker.

As discussed in a recent review (Reddy and Beal; "*Amyloid beta, mitochondrial dysfunction and synaptic damage: implications for cognitive decline in aging and Alzheimer's disease*"; Trends in Molecular Medicine, Vol. 14 No. 2 (2008)), Aβ is known to localize to mitochondria and to cause mitochondrial damage. This intracellular Aβ and its toxic effect particularly on mitochondria are discussed as a rather early event during the progression of AD.

As noted above, there is no cure for AD; it appears only possible to alleviate some of the symptoms or to delay the onset of the disease. It is noteworthy in this respect that there are hints that anti-inflammatory agents and/or anti-oxidants can be beneficial for inhibiting or delaying the onset of AD since patients suffering from arthritis and treated with anti-inflammatory agents show a reduced rate of AD. This beneficial effect might particularly occur if AD patients are treated with anti-inflammatory agents or anti-oxidants at an early stage of the disease (see Marty "*Anti-inflammatory drugs and Alzheimer's disease*"; BMJ 2003; 327:353 and Breitner et al. "*Extended results of the Alzheimer's disease anti-inflammatory prevention trial*"; Alzheimers Dement. 2011; 7(4):402-411).

As is evident from the above, there is a strong need for markers indicating AD and methods of diagnosing AD, particularly in a living subject and at an early stage of AD. Furthermore, there is a strong need for developing effective medicaments against AD and for screening compounds for their activity against AD.

OBJECTS AND SUMMARY OF THE INVENTION

The inventors of the present invention have surprisingly found that Aβ, which is present in cells and in particular in mitochondria of AD patients not only inhibits PreP, the mitochondrial peptidase responsible for degradation of signaling peptides, but also MPP, the mitochondrial peptidase responsible for the removal of mitochondrium-targeting presequences. In consequence, Aβ thus results in an accumulation of mitochondrial precursor and precursor processing intermediate proteins and such proteins may thus be used as markers for AD.

In a first aspect, the present invention relates to a method of diagnosing AD in a patient comprising the following steps:
  a) Providing a sample from a patient potentially suffering from AD;
  b) Determining the amount of at least one premature mitochondrial protein in said sample, wherein said premature mitochondrial protein comprises at least part of its mitochondrium-targeting presequence; and
  c) Comparing the amount obtained in step b) to the amount of said at least one premature mitochondrial protein determined in a control sample, wherein said control sample is derived from a subject not suffering from AD;
wherein a higher amount of said at least one premature mitochondrial protein in the sample from a patient potentially suffering from AD compared to the amount of said at least one premature mitochondrial protein in the control sample indicates AD in said patient.

This method may also be formulated as method of diagnosing AD in a patient comprising the following steps:
  a) Providing a sample from a patient potentially suffering from AD;
  b) Determining the amount m1 of at least one premature mitochondrial protein in said sample, wherein said premature mitochondrial protein comprises at least part of its mitochondrium-targeting presequence; and
  c) Comparing the amount m1 obtained in step b) to the amount m2 of said at least one premature mitochondrial protein determined in a control sample, wherein said control sample is derived from a subject not suffering from AD;
wherein m1>m2 indicates AD in said patient.

In a first embodiment relating to the first aspect, the method is an in vitro method.

In another embodiment, an early stage of AD is diagnosed.

In yet another embodiment, said sample is provided outside the human or animal body. It is noted that the step of obtaining the sample from a living patient (particularly a living human patient) is not part of the method as claimed.

In a preferred embodiment, said sample is a clinical sample, wherein said clinical sample is preferably from a human patient. It can be preferred that said clinical sample is a tissue sample or a body fluid sample. It is particularly preferred that a sample is used, which comprises cells comprising mitochondria (such as e.g. a blood sample).

Said sample may e.g. be a tissue sample gained from the respiratory tract, the gastrointestinal tract or the brain. Said tissue sample may also be obtained from skin, wherein said skin sample comprises fibroblasts. A tissue sample gained from the brain can be preferred if the method is carried out post mortem (i.e. after the patient has died). However, tissue samples can of course also be used if the patient to be diagnosed is a living human or animal patient. A preferred sample in this respect is a skin sample comprising skin fibroblasts, wherein such skin fibroblasts are optionally isolated and/or optionally cultivated according to standard methods in order to increase the cell number.

Further, said sample may in particular be a body fluid sample selected from the group consisting of blood, plasma, serum, lymphatic fluid, saliva, cerebrospinal fluid, urine and feces, wherein blood is preferred. All of the above-mentioned body fluids, in particular blood, are particularly preferred if the patient to be diagnosed is a living human or animal patient.

It is particularly preferred to use a blood sample or a brain sample. When the patient to be diagnosed is a living human or animal patient, it is particularly preferred to use a blood sample or a skin sample.

In another embodiment of the first aspect, the amount of said at least one premature mitochondrial protein is determined by an immunological method, preferably Western-Blot or ELISA, and/or by a mass-spectrometry (MS) method, in particular combined fractional diagonal chromatography (COFRADIC; see Gevaert et al., Nat. Biotech 21, 566 (2002)), charge-based fractional diagonal chromatography (CHAFRADIC; see Venne et al., J. Proteome Res. 12, 3823 (2013) and terminal amine isotopic labeling of substrates (TAILS; see Kleifeld et al., Nat. Biotech. 28, 281 (2010)). Further, phospho tagging (PTAC) may also be used, see Mommen G P et al., Mol Cell Proteomics 11(9) (2012). It is noted that COFRADIC is particularly preferred since this method is particularly suitable for determining the N-termini of proteins.

In a preferred embodiment relating to the first aspect, said at least one premature mitochondrial protein comprises said at least part of its mitochondrium-targeting presequence at its N-terminus; said protein may be a nucleus-encoded protein.

In another preferred embodiment relating to the first aspect, said at least one premature mitochondrial protein is selected from the group consisting of hMdh2, hOAT, hACADV, PMPCA, CLYBL, PPM1K, SLIRP, NDUFA9, MRPL23 and mixtures thereof. HMdh2 is particularly preferred. In a preferred embodiment, hMdh2 is the only premature mitochondrial protein, the amount of which is determined. It is understood that the above listed mitochondrial proteins correspond to premature versions of the mature forms, i.e. all of these proteins still comprise at least part of their mitochondrium-targeting presequence at their N-termini of the mature forms. The mitochondrium-targeting presequences of the above mentioned proteins are given below.

In yet another preferred embodiment, the amount of said at least one premature mitochondrial protein determined in a control sample corresponds to a predetermined value derived from at least one, preferably several control samples. Thus, the amount may be provided as predetermined value from a corresponding list of control amounts. It is noted that it can be preferred that said subject not suffering from AD matches about the age of the patient potentially suffering from AD. However, this is not a prerequisite for the comparison step.

In still another preferred embodiment, more than about a 5%, preferably more than about a 10%, more preferably more than about a 20% and most preferably more than about a 50% increase of the amount of said at least one premature mitochondrial protein in the sample from the patient potentially suffering from AD compared to the amount of said at least one premature mitochondrial protein in the control sample corresponds to a higher amount.

As described below in the detailed description section, a "higher amount" can also mean that said protein is present in said sample from a patient potentially suffering from AD and absent in the control sample. Thus, in a preferred embodiment, the first aspect of the invention also relates to a method of diagnosing AD in a patient comprising the following steps:
  a) Providing a sample from a patient potentially suffering from AD;
  b) Determining the presence or absence of at least one premature mitochondrial protein selected from the group consisting of hMdh2, hOAT, hACADV, PMPCA, CLYBL, PPM1K, SLIRP, NDUFA9, MRPL23 and mixtures thereof in said sample, wherein said premature protein comprises at least part of its mitochondrium-targeting presequence;
wherein the presence of said premature protein in said sample indicates AD in said patient.

In a particularly preferred embodiment, the first aspect of the present invention relates to a method of diagnosing AD in a patient comprising the following steps:
  c) Providing a sample from a patient potentially suffering from AD;
  d) Determining the presence or absence of premature hMdh2 in said sample, wherein said premature hMdh2 comprises at least part of its mitochondrium-targeting presequence;
wherein the presence of premature hMdh2 in said sample indicates AD in said patient.

In a related embodiment of the first aspect, the present invention also relates to a method of substantiating the diagnosing of AD in a patient comprising the following steps:
  a) Providing a sample from a patient diagnosed as suffering from AD, wherein said diagnosis is preferably based on a different method than the method disclosed herein;
  b) Determining in said sample the amount of at least one premature mitochondrial protein, wherein said premature mitochondrial protein comprises at least part of its mitochondrium-targeting presequence; and
  c) Comparing the amount obtained in step b) to the amount of said at least one premature mitochondrial protein determined in a control sample, wherein said control sample is derived from a subject not suffering from AD;
wherein a higher amount of said at least one premature mitochondrial protein in the sample from a patient diagnosed as suffering from AD compared to the amount of said at least one premature mitochondrial protein in the control sample substantiates (i.e. confirms) the diagnosis of AD in said patient.

In accordance with the above, the first aspect of the invention further relates to a method of substantiating the diagnosis of AD in a patient comprising the following steps:
  a) Providing a sample from a patient potentially suffering from AD, wherein said diagnosis is preferably based on a different method than the method disclosed herein;
  b) Determining the presence or absence of at least one premature mitochondrial protein selected from the group consisting of hMdh2, hOAT, hACADV, PMPCA, CLYBL, PPM1K, SLIRP, NDUFA9, MRPL23 and mixtures thereof in said sample, wherein said premature protein comprises at least part of its mitochondrium-targeting presequence;
wherein the presence of said premature protein in said sample substantiates (i.e. confirms) the diagnosis of AD in said patient.

Accordingly, in another related preferred embodiment of the first aspect, the present invention also relates to a method of substantiating the diagnosing of AD in a patient comprising the following steps:
  a) Providing a sample from a patient diagnosed as suffering from AD, wherein said diagnosis is preferably based on a different method than the method disclosed herein;
  b) Determining the presence or absence of premature hMdh2 in said sample, wherein said premature hMdh2 comprises at least part of its mitochondrium-targeting presequence;
wherein the presence of premature hMdh2 in said sample substantiates (i.e. confirms) the diagnosis of AD in said patient.

In a second aspect, the present invention relates to the use of at least one premature mitochondrial protein as marker for AD, wherein said at least one premature mitochondrial protein comprises at least part of the mitochondrial-targeting presequence.

In a preferred embodiment of the second aspect of the present invention, said at least one premature mitochondrial protein is selected from the group consisting of hMdh2, hOAT, hACADV, PMPCA, CLYBL, PPM1K, SLIRP, NDUFA9, MRPL23 and mixtures thereof. It is understood that the above listed mitochondrial proteins correspond to premature versions of the mature forms, i.e. all of these proteins still comprise at least part of their mitochondrial-targeting presequence at their N-termini of the mature forms. These N-terminal presequences are given below.

In a particularly preferred embodiment of the second aspect, said at least one premature mitochondrial protein is hMdh2.

In a third aspect, the present invention is concerned with the use of an antibody or a binding fragment thereof binding to a mitochondrial protein for diagnosing AD. It can be preferred to use an antibody or a binding fragment thereof binding to a nucleus-encoded mitochondrial protein for diagnosing AD.

In a first embodiment of the third aspect, said antibody or a binding fragment thereof binds to the mature form of said mitochondrial protein. Clearly, premature forms of the mature forms can also be detected with such an antibody since the mitochondrium-targeting presequence is present at the N-terminus of the mature form of the protein. It needs to be understood that, if an antibody or a binding fragment thereof binding to the mature form is used for diagnosing AD, it can be of particular importance to analyze shifts in the molecular weight of the protein starting from the molecular weight of the mature form towards higher molecular weights due to the additional molecular weight of the mitochondrium-targeting presequence, which is at least partly present.

In a second embodiment of the third aspect, said antibody or binding fragment thereof binds to the premature form of said mitochondrial protein, wherein said premature mitochondrial protein comprises at least part of the mitochondrial-targeting presequence. Preferably, such an antibody or binding fragment thereof binds to the N-terminal domain of such a premature form and most preferably to the mitochondrium-targeting presequence (or parts thereof) of said mitochondrial protein. Most preferably, such an antibody or binding fragment thereof recognizes only the premature form of said mitochondrial protein and not the mature form. Antibodies or binding fragments according to this embodiment can be particularly preferred in the present invention and are described in further detail in the fourth aspect of the present invention. Thus, e.g. the antibody directed to the presequence of hMdh2 as described in the fourth aspect of the invention and in example 1 of the present application is a particularly suitable example of such an antibody and may be used in the third aspect of the present invention.

In the third embodiment of the third aspect, said antibody or binding fragment thereof binds both, the mature part of said mitochondrial protein and the additional sequence of the mitochondrium-targeting presequence (or parts thereof) at the N-terminus of the mature part.

In a preferred embodiment, said antibody or binding fragment thereof binds to a mitochondrial protein selected from the group consisting of hMdh2, hOAT, hACADV, PMPCA, CLYBL, PPM1K, SLIRP, NDUFA9 and MRPL23, wherein said protein may be in its premature form or in its mature forms, depending on what type of antibody or binding fragment thereof is used. Thus, it is noted that the above recited three embodiments also apply to the antibody or binding fragment thereof binding to the specific proteins listed above and that commercially available antibodies or binding fragments thereof may be used.

In a particularly preferred embodiment, said antibody or binding fragment thereof binds to hMdh2. It is noted that the above recited three embodiments also apply to the antibody or binding fragment thereof binding to hMdh2 (i.e. either directed to the mature form of hMdh2, directed to the N-terminal presequence only or directed to both, the N-terminal presequence and the mature part of the protein) and that commercially available antibodies may be used.

In a fourth aspect, the present invention relates to an antibody or a binding fragment thereof binding to a peptide or fragment thereof selected from the group consisting of MLSALARPASAALRRSFSTSAQNN (SEQ ID No.: 20), MFSKLAHLQRFAVLSRGVHSSVASATSVATKKTVQ (SEQ ID No.: 21), MQAARMAASLGRQLLRLGGGSSR-LTALLGQPRPGPARRPY (SEQ ID No.: 22), MAAVV-LAATRLLRGSGSWGCSRLRFGPPAYRRF (SEQ ID No.: 23), MALRLLRRAARGAAAAALLRLK (SEQ ID No.: 24), MSTAALITLVRSGGNQVRRRVLLSSRLLQ (SEQ ID No.: 25), MAASAARGAAALRRSINQPVAFVRRIPW (SEQ ID No.: 26), MAAAAQSRVVRVLSMSRSAITA-IATSVCHGPPCRQ (SEQ ID No.: 69), and MARNVVY-PLYRLGGPQLRVFRT (SEQ ID No.: 70)

The antibody may be a monoclonal or polyclonal antibody and can be produced by any common means for generating antibodies using the mentioned peptide or a fragment thereof as antigen. The binding fragment may be derived from a monoclonal or polyclonal antibody and can also be produced according to standard methods known in the art.

In a preferred embodiment of the fourth aspect, a fragment of a peptide as listed above (selected from SEQ ID No.: 20 to 26) comprises about 21, about 20, about 19, about 18, about 17, about 16, about 15, about 14, about 13, about 12, about 11 or about 10 amino acids starting from the N-terminus of said peptide. Thus, by way of example, the peptide MLSALARPASAALRRSFST (SEQ ID No.: 31) corresponds to a fragment of the peptide of SEQ ID No.: 20, wherein said fragment comprises 19 amino acids starting from the N-terminus of the peptide of SEQ ID No.: 20. It is further preferred that a fragment comprises at least 10 amino acids, more preferably at least 15 amino acids.

In an especially preferred embodiment of the fourth aspect, said antibody or binding fragment thereof binds to peptide MLSALARPASAALRRSFSTSAQNN (SEQ ID No.: 20) or a fragment thereof, wherein said fragment can be selected from the group consisting of MLSALARPASAAL-RRSFSTSAQN (SEQ ID No.: 27), MLSALARPASAAL-RRSFSTSAQ (SEQ ID No.: 28), MLSALARPASAAL-RRSFSTSA (SEQ ID No.: 29), MLSALARPASAALRRSFSTS (SEQ ID No.: 30), MLSALARPASAALRRSFST (SEQ ID No.: 31), MLSALARPASAALRRSFS (SEQ ID No.: 32), MLSALA-RPASAALRRSF (SEQ ID No.: 33), MLSALARPASAAL-RRS (SEQ ID No.: 34), MLSALARPASAALRR (SEQ ID No.: 35), MLSALARPASAALR (SEQ ID No.: 36), MLSALARPASAAL (SEQ ID No.: 37) and MLSALAR-PASAA (SEQ ID No.: 38).

Most preferably, the antibody or binding fragment thereof of the fourth aspect of the present invention is an antibody or binding fragment thereof binding to the peptide MLSALARPASAALRRSFST (SEQ ID No.: 31). A polyclonal antibody directed against said peptide has been raised by the inventors according to standard procedures known in the art, and is discussed in further detail in the example section of the present application.

In another preferred embodiment of the fourth aspect, said antibody or binding fragment thereof binds to peptide MFSKLAHLQRFAVLSRGVHSSVASATSV ATKKTVQ (SEQ ID No.: 21) or a fragment thereof, wherein said fragment can be selected from the group consisting of MFSKLAHLQRFAVLSRGVHSSVASATSV ATKKTV (SEQ ID No.: 39), MFSKLAHLQRFAVLSRGVHSS-VASATSVATK (SEQ ID No.: 40), MFSKLAHLQRFAV-LSRGVHSSVASATSV (SEQ ID No.: 41), MFSKLAHL-QRFAVLSRGVHSSVA (SEQ ID No.: 42) and MFSKLAHLQRFAVLSR (SEQ ID No.: 43).

In another preferred embodiment of the fourth aspect, said antibody or binding fragment thereof binds to peptide MQAARMAASLGRQLLRLGGGSSRLTALL GQPRPG-PARRPY (SEQ ID No.: 22) or a fragment thereof, wherein said fragment can be selected from the group consisting of MQAARMAASLGRQLLRLGGGSSR LTALLGQPRPG (SEQ ID No.: 44), MQAARMAASLGRQLLRLGGGSSR-LTA LLGQP (SEQ ID No.: 45), MQAARMAASLGRQLL-RLGGGSSRLTALL (SEQ ID No.: 46), MQAAR-MAASLGRQLLRLGGGSSR (SEQ ID No.: 47) and MQAARMAASLGRQL (SEQ ID NO.: 48).

In another preferred embodiment of the fourth aspect, said antibody or binding fragment thereof binds to peptide MAAVVLAATRLLRGSGSWGCSRLR FGPPAYRRF (SEQ ID No.: 23) or a fragment thereof, wherein said fragment can be selected from the group consisting of MAAVVLAATRLLRGSGSWGCSRLRFGP (SEQ ID No.: 49), MAAVVLAATRLLRGSGSWGCSRLRFG (SEQ ID No.: 50), MAAVVLAATRLLRGSGSWGCSRLRF (SEQ ID No.: 51), MAAVVLAATRLLRGSGSWGCSRLR (SEQ ID No.: 52) and MAAVVLAATRLLRGSGSWGCSRL (SEQ ID No.: 53).

In another preferred embodiment of the fourth aspect, said antibody or binding fragment thereof binds to peptide MAL-RLLRRAARGAAAAALLRLK (SEQ ID No.: 24) or a fragment thereof, wherein said fragment can be selected from the group consisting of MALRLLRRAAR-GAAAAALLRL (SEQ ID No.: 54), MALRLLRRAAR-GAAAAALLR (SEQ ID No.: 55), MALRLLRRAAR-GAAAA ALL (SEQ ID No.: 56), MALRLLRRAARGAAAAAL (SEQ ID No.: 57), and MALRLLRRAARGAAAAA (SEQ ID No.: 58).

In another preferred embodiment of the fourth aspect, said antibody or binding fragment thereof binds to peptide MSTAALITLVRSGGNQVRRRVLLSSRLLQ (SEQ ID No.: 25) or a fragment thereof, wherein said fragment can be selected from the group consisting of MSTAAL-ITLVRSGGNQVRRRVLLSSR (SEQ ID No.: 59), MSTAALITLVRSGGNQVRRRVLLS (SEQ ID No.: 60), MSTAALITLVRSGGN QVRRRVL (SEQ ID No.: 61), MSTAALITLVRSGGNQVRRR (SEQ ID No.: 62), and MSTAALITLVRSGGNQVRR (SEQ ID No.: 63). A particularly preferred fragment is MSTAALITLVRSGGNQVRRR (SEQ ID No.: 62).

In another preferred embodiment of the fourth aspect, said antibody or binding fragment thereof binds to peptide MAASAARGAAALRRSINQPVAFVRRIPW (SEQ ID No.: 26) or a fragment thereof, wherein said fragment can be selected from the group consisting of MAASAARGAAAL-RRSINQPVAFV (SEQ ID No.: 64), MAASAARGAAAL-RRSINQPVAF (SEQ ID No.: 65), MAASAARGAAAL-RRSIN (SEQ ID No.: 66), MAASAARGAAALRRSI (SEQ ID No.: 67), and MAASAARGAAALRR (SEQ ID No.: 68).

In another preferred embodiment of the fourth aspect, said antibody or binding fragment thereof binds to peptide MAAAAQSRVVRVLSMSRSAITAIATSV CHGPPCRQ (SEQ ID No.: 69) or a fragment thereof, wherein said fragment can be selected from the group consisting of MAAAAQSRVVRVLSMSRSAITAIATSVCH (SEQ ID No.: 71), MAAAAQSRVVRVLSMSRSAITAIA (SEQ ID No.: 72), MAAAAQSRVVRVLSMSRSAI (SEQ ID No.: 73), MAAAAQSRVVRVLSMSRS (SEQ ID No.: 74) and MAAAAQSRVVRVLSMS (SEQ ID No.: 75). A particularly preferred fragment is MAAAAQSRVVRVLSMSRS (SEQ ID No.: 74).

In another preferred embodiment of the fourth aspect, said antibody or binding fragment thereof binds to peptide MARNVVYPLYRLGGPQLRVFRT (SEQ ID No.: 70) or a fragment thereof, wherein said fragment can be selected from the group consisting of MARNVVYPLYRLGGPQL-RVFR (SEQ ID No.: 76), MARNVVYPLYRLGGPQLRVF (SEQ ID No.: 77), MARNVVYPLYRLGGPQLRV (SEQ ID No.: 78), MARNVVYPLYRLGGPQLR (SEQ ID No.: 79) and MARNVVYPLYRLGGPQL (SEQ ID No.: 80).

An antibody or a binding fragment thereof of the fourth aspect of the present invention may particularly be employed in the use described in the third aspect.

In a fifth aspect, the present invention relates to an anti-inflammatory agent and/or an antioxidant for use in the treatment of AD, wherein said anti-inflammatory agent and/or antioxidant is administered to a patient displaying a higher amount of at least one premature mitochondrial protein in a sample (m1) compared to the amount (m2) of said protein in a control sample derived from a subject not suffering from AD (may also be referred to as m1>m2), wherein said premature mitochondrial protein comprises at least part of the mitochondrial-targeting presequence.

A preferred embodiment of the fifth aspect is concerned with an anti-inflammatory agent and/or an antioxidant for use in the treatment of AD, wherein said anti-inflammatory agent and/or antioxidant is administered to a patient having premature hMdh2 present in a sample, wherein said premature hMdh2 comprises at least part of its mitochondrium-targeting presequence.

In an embodiment of the fifth aspect, said anti-inflammatory agent and/or said antioxidant is for use in the treatment of an early stage of AD.

In another embodiment, said anti-inflammatory agent is a non-steroidal anti-inflammatory agent (such as e.g. ibuprofen or indomethacin). In yet another preferred embodiment, said antioxidant is selected from the group consisting of ascorbic acid, fatty esters, isomers and salts thereof (including sodium ascorbate and calcium ascorbate); tocopherole; gallic acid derivatives; lecithine; lactate and salts thereof; citric acid and salts thereof; tartrate and salts thereof; and phosphoric acid and salts thereof.

In still another preferred embodiment of the fifth aspect, more than about a 5%, preferably more than about a 10%, more preferably more than about a 20% and most preferably more than about a 50% increase of the amount of said at least one premature mitochondrial protein in the sample from the patient compared to the amount of said at least one premature mitochondrial protein in the control sample corresponds to a higher amount.

Said sample may e.g. be a tissue sample gained from the skin, respiratory tract, the gastrointestinal tract or from the brain. A tissue sample gained from the brain can be preferred if the method is carried out post mortem, i.e. after the patient has died. However, tissue samples and in particular skin samples can of course also be used if the patient to be diagnosed is a living human or animal patient.

Further, said sample may in particular be a body fluid sample selected from the group consisting of blood, plasma, serum, lymphatic fluid, saliva, cerebrospinal fluid, urine and feces, wherein blood is preferred. All of the above-mentioned body fluids, in particular blood, are particularly preferred if the patient to be diagnosed is a living human or animal patient.

It is particularly preferred to use a blood sample or a brain sample. When the patient to be diagnosed is a living human or animal patient, it is particularly preferred to use a blood or skin sample.

In a sixth aspect, the present invention is concerned with a method of screening for a compound effective against AD comprising the following steps:
  a) Providing an assay system comprising a compromised mitochondrial PreP, wherein said compromised mitochondrial PreP results in an accumulation of at least one premature mitochondrial protein, wherein said premature mitochondrial protein comprises at least part of its mitochondrial-targeting presequence;
  b) Determining the amount of said at least one premature mitochondrial protein;
  c) Contacting said assay system with a compound;
  d) Determining the amount of said at least one premature mitochondrial protein;
wherein a lower amount of said at least one premature mitochondrial protein determined in step d) compared to the amount determined in step b) indicates that said compound is effective against AD.

In an alternative embodiment, the sixth aspect of the present invention is concerned with a method of screening for a compound effective against AD comprising the following steps:
  a) Providing an assay system comprising a compromised mitochondrial PreP, wherein said compromised mitochondrial PreP results in an accumulation of at least one premature mitochondrial protein, wherein said premature mitochondrial protein comprises at least part of its mitochondrial-targeting presequence;
  b) Determining the amount of reactive oxygen species (ROS) in said system;
  c) Contacting said assay system with a compound;
  d) Determining the amount of ROS in said system;
wherein a lower amount of ROS determined in step d) compared to the amount determined in step b) indicates that said compound is effective against AD.

In yet another alternative embodiment, the sixth aspect of the present invention is concerned with a method of screening for a compound effective against AD comprising the following steps:
  a) Providing an assay system comprising a compromised mitochondrial PreP, wherein said PreP has been compromised by the addition of A$\beta$ and said compromised mitochondrial PreP results in an accumulation of at least one premature mitochondrial protein, wherein said premature mitochondrial protein comprises at least part of its mitochondrial-targeting presequence;
  b) Determining the amount of A$\beta$ in said system;
  c) Contacting said assay system with a compound;
  d) Determining the amount of A$\beta$ in said system;
wherein a lower amount of A$\beta$ determined in step d) compared to the amount determined in step b) indicates that said compound is effective against AD.

It can be preferred in the latter alternative that A$\beta$ is added to the assay system by expressing a preform of A$\beta$ comprising a recognition site for the TEV-protease, which is then cleaved by TEV-protease upon induction of expression of said TEV-protease.

In an embodiment relating to the above alternatives of the sixth aspect, said assay system provided in step a) is an in vitro system or a cell culture system or an at least partly reconstituted in vitro system. The example section of the present applications sets out assays, which may be used in the sixth aspect. The skilled person is aware of how to use similar assay systems in the sixth aspect.

In a preferred embodiment of the sixth aspect, said assay system provided in step a) comprises mitochondria isolated from human cell culture cells or yeast cells.

In a preferred embodiment of the sixth aspect, human cell culture cells are used in a cell culture system. In another preferred embodiment, yeast cells are used in a cell culture system, wherein said yeast cells preferably express A$\beta$ in an inducible manner. An exemplary system of such yeast cells is set out in the example section of the present application. Thus, said assay system of step a) may comprise yeast cells in which A$\beta$ can be preferably inducibly generated using inducible TEV protease.

It can further be preferred to use yeast cells, which have been manipulated according to methods known to the skilled person to allow for an easier penetration of the compound added to the system.

In another preferred embodiment of the sixth aspect, said compound is a small molecule. In yet another preferred embodiment of the sixth aspect, said compound exhibits activating activity on MPP and/or increases the half life of MPP.

In yet another embodiment, the assay system as referred to above is incubated for a specific time after the step of contacting said assay system with a compound and the subsequent step. This incubation time may vary from several minutes to several hours to several days depending on the assay system used. Thus, the incubation time may e.g. be 10 minutes, 40 minutes, 1 hour, 2 hours, 5 hours, 1day, 3 days or even 5 days. It is particularly preferred to use an incubation time of about 1 hour.

In the above methods of screening, the amount of said at least one premature mitochondrial protein may be determined according to the methods as set out in the first aspect of the present application, whereas the amount of Aβ is typically determined by immunological methods as set out above. The amount of ROS as determined in the second alternative described in the sixth aspect of the invention may be determined by standard methods, e.g. using dihydroethidium (DHE) staining.

In still another embodiment of the sixth aspect, more than about a 5%, preferably more than about a 10%, more preferably more than about a 20% and most preferably more than about a 50% decrease of the amount determined in step d) compared to the amount in step b) corresponds to a lower amount.

DETAILED DESCRIPTION OF THE INVENTION

Figure 1:
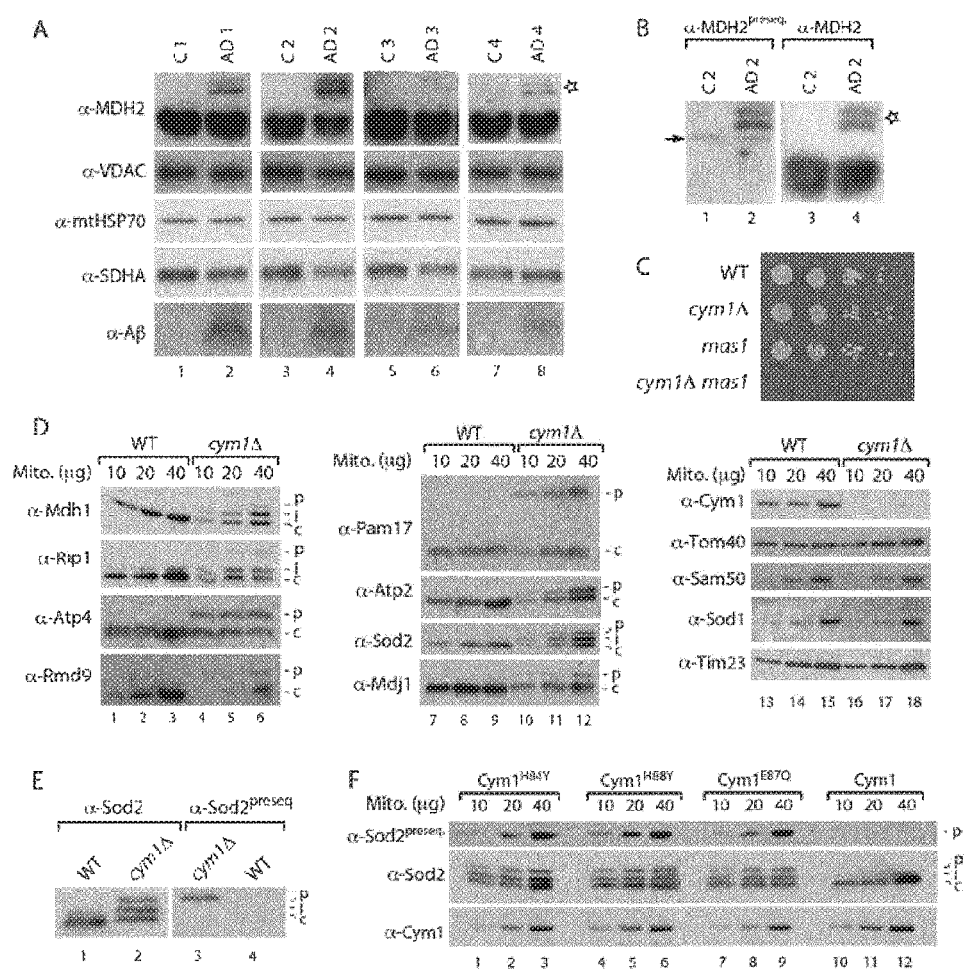
FIG. 1. In vivo accumulation of precursor proteins and processing intermediates in mitochondria from AD patients and peptidasome-deficient (cym1Δ) yeast mutant. (A) Immunoblot analysis of various mitochondrial proteins in purified brain (temporal cortex) mitochondria from AD and age-matched non-AD control brains (isolated pairwise). Star indicates precursor protein. (B) Validation of MDH2 precursor accumulation (star) in AD brain mitochondria using presequence specific antibody. Arrow, non-specific signal. (C) Synthetic lethality of cym1Δ mas1 double mutant under respiratory growth condition (30° C., YPG). (D) Immunoblot analysis of wild-type (WT) and cym1Δ mitochondria isolated from yeast strains grown on YPD at 30° C. Right panel shows Cym1 and non-processed proteins as controls. (E) Sod2 presequence specific antibody recognizes the larger precursor form accumulating in cym1Δ mitochondria. (F) Immunoblot showing Sod2 precursor accumulation in yeast with mutations in the catalytic center of Cym1 (HXXEH). p, precursor; i, intermediate; c, cleaved protein.

The present invention is based on the surprising finding that the mitochondrial protease MPP is functionally coupled to the mitochondrial protease PreP such that an inhibition of PreP by Aβ leads to the inhibition of MPP. By consequence, mitochondrial precursor and intermediate precursor proteins accumulate. Thus, increased amounts of mitochondrial precursor and intermediate precursor proteins are indicative for the presence of Aβ in mitochondria, which is characteristic for AD, particularly for an early stage of AD.

Before the present invention is described in more detail, the following definitions are introduced.

1. Definitions

As used in the specification and the claims, the singular forms of "a" and "an" also include the corresponding plurals unless the context clearly dictates otherwise.

The term "about" in the context of the present invention denotes an interval of accuracy that a person skilled in the art will understand to still ensure the technical effect of the feature in question. The term typically indicates a deviation from the indicated numerical value of ±10% and preferably ±5%.

It needs to be understood that the term "comprising" is not limiting. For the purposes of the present invention, the term "consisting of" is considered to be a preferred embodiment of the term "comprising". If hereinafter a group is defined to comprise at least a certain number of embodiments, this is also meant to encompass a group which preferably consists of these embodiments only. Likewise, if an isolated polypeptide is defined as comprising a specific sequence, this is also meant to encompass an isolated polypeptide which preferably consists of this specific sequence.

Unless defined otherwise, all technical and scientific terms used herein have the meanings as commonly understood by a skilled person. Thus, e.g. the term "Alzheimer's disease" or "AD" as used herein refers to the disease including all symptoms (particularly dementia) as known to the skilled person.

The term "diagnosing AD in a patient" as used herein means that the presence or absence of AD in a patient is determined. Thus, if the method of the present invention indicates a higher amount of said at least one premature mitochondrial protein in the sample from a patient potentially suffering from AD compared to the amount of said at least one premature mitochondrial protein in the control sample, the diagnosis of AD in said patient is positive (i.e. AD is present). If the method of the present invention fails to indicate a higher amount of said at least one premature mitochondrial protein in the sample from a patient potentially suffering from AD compared to the amount of said at least one premature mitochondrial protein in the control sample, the diagnosis of AD in said patient is negative (i.e. AD is not present). "Diagnosing AD" is thus not necessarily connected to a positive diagnosis.

The term "patient" as used herein refers to a human or veterinary subject. Furthermore, the term includes both, living and dead patients.

As used herein, the term "sample" refers to any biological sample from any human or veterinary subject. The samples may include tissues obtained from any organ, such as e.g. the brain and skin, and fluids obtained from any organ such as e.g. the blood, plasma, serum, lymphatic fluid, synovial fluid, cerebrospinal fluid, amniotic fluid, amniotic cord blood, tears, saliva, and nasopharyngeal washes. A brain sample, a skin sample, a blood sample and a cerebrospinal fluid sample are particularly preferred for the present invention. As noted above, a brain sample may particularly be provided if the patient is dead, whereas a blood sample may particularly be provided if the patient is alive. It is noted that a tissue sample (e.g. from the respiratory trast, the gastrointestinal tract, the skin or a muscle) of a living patient may of course also be provided. As regards samples differing from a brain sample and in particular as regards a blood sample, it is noted that mitochondrial dysfunctions in AD have not only been described for cells from the brain but also for peripheral cells, in particular blood cells comprising e.g. lymphocytes (see Leuner et al., 2012).

If reference is made to a "clinical sample", this indicates that the sample is handled according to standard proceedings used for samples in a clinical background, e.g. in hospitals or a medical practice.

The term "potentially suffering from AD" as used in the present invention means that a patient has not yet been positively diagnosed with AD, e.g. by a histological analysis of brain tissue post mortem. The "patient potentially suffering from AD" may be naïve with respect to initial observations as regards AD or may be a patient, who is already generally suspicious of suffering from AD, e.g. from a corresponding AD history of relatives, from cognitive tests or from imaging methods.

The term "determining the amount" as used herein means that the amount of at least one protein is determined in relation to a second parameter such as e.g. the volume of a sample or the amount of cells in the sample or the presence of a different protein used as internal standard. This means that the amount is always normalized to a second parameter. Thus, the amount may e.g. correspond to a concentration if the second parameter is the volume. It is to be understood that the amount of the at least one protein determined in the control sample is also normalized to a second parameter, e.g. the parameters set out above. The skilled person understands that a comparison step as described herein is only possible if both amounts are normalized. The term "determining the amount" does not exclude that no such protein at all can be detected in a sample—this particularly applies to a protein, the amount of which is determined in a control sample. Thus, a protein found in a sample from a patient potentially suffering from AD (the amount of which is determined) may not be present at all in a control sample.

For the present application, the term "mitochondrial protein" in particular relates to any nucleus-encoded protein, the gene of which is transcribed into mRNA in the nucleus, followed by the translation of the mRNA in the ribosome and subsequent release into the cytosol and the import into the mitochondrium. However, also mitochondrium-encoded proteins with a targeting sequence are encompassed by this term. Thus, a "mitochondrial protein" initially comprises a mitochondrium-targeting sequence. This sequence is normally cleaved off after successful import into a mitochondrium and/or a specific compartment therein, respectively. As used herein, the term does not relate to proteins, which completely lack any type of mitochondrium-targeting sequence.

The term "premature" used in combination with "mitochondrial protein" means that the amino acid sequence does not correspond to the amino acid sequence of the mature mitochondrial protein; thus, at least part of the mitochondrium-targeting sequence is still present at the N-terminus of the mature sequence of the protein. It needs to be understood that "premature" as used herein does not mean that the complete mitochondrium-targeting sequence needs to be present at the N-terminus of the mature sequence of the protein. For this reason, several premature forms of a single mitochondrial protein may be present, wherein each form may comprise a mitochondrium-targeting sequence of a different length.

The term "mitochondrium-targeting presequence" as used herein relates to a targeting sequence for nucleus-encoded mitochondrial proteins or for mitochondrium-encoded mitochondrial proteins, wherein said targeting sequence is found at the N-termini of said mitochondrial proteins after translation and prior to/during import into a mitochondrium or a compartment thereof, respectively. The targeting sequence for nucleus-encoded mitochondrial proteins is usually between about 10 and about 80 amino acids in length and it is assumed that the targeting sequence forms an amphiphatic α-helix, in which positively charged amino acid side chains are located at one side of the helix, whereas uncharged polar amino acid side chains are located at the other side of the helix. It is emphasized that there is no unique mitochondrium-targeting sequence, which is found in exactly this sequence at the N-termini of all proteins targeted to the mitochondria. Rather, the above mentioned functional aspects of the sequence appear to be essential such that no unique order of amino acids appears to be required. For this reason, it is e.g. not possible to detect all premature mitochondrial proteins by a single antibody.

The term "at least part of the mitochondrium-targeting (pre)sequence" means that said sequence has not been completely removed. Thus, said sequence can still be comprised as complete sequence (see above) or lack at least 1, 2, 3, 4, 5, 6, 7 or 8 amino acids from the N-terminus of the complete presequence. Depending on the length of the presequence, of course also more than 8 amino acids can be removed by initial cleavage, wherein a part of this presequence would then still be present.

The term "comparing" as used herein means that the amount determined in step b) is compared to an amount derived from a control sample, wherein the amount of the control sample ("control amount") must not necessarily be determined in parallel. The "control amount" may also be derived from a list comprising at least one predetermined value, which has been obtained from previous determinations with at least one control sample, preferably with several control samples, such as e.g. 10, 50, 100, 1000 or 10000 control samples. It can be preferred to obtain such predetermined control values from subjects not suffering from AD in connection with at least one further parameter, such as e.g. the age and/or the sex; if age-dependent predetermined control values are at hand, the age of the patient potentially suffering from AD may be aligned with a predetermined control value derived from subjects of the same age. It can be preferred to determine control values starting from the age of 40 years. The above comments regarding a normalization also apply to the control.

The term "higher amount" as used herein means that the amount of the at least one premature mitochondrial protein in the sample from the patient potentially suffering from AD is increased compared to the amount of said at least one premature mitochondrial protein in the control sample by more than 5%, preferably by more than 10%, more preferably by more than 20% and most preferably by more than 50%. If said premature mitochondrial protein should not be detectable at all in the control sample, the presence of said premature mitochondrial protein in the sample from the patient potentially suffering from AD is indicative of AD. Thus, the term "higher amount" can also refer to a situation wherein said protein is present in the sample from a patient potentially suffering from AD and absent in the control sample.

The term "antibody" as used herein preferably relates to a monoclonal or polyclonal antibody. However, the antibody may also be selected from antibody variants or fragments such as e.g. single chain antibodies, diabodies, minibodies, single chain Fv fragments (sc(Fv)), sc(Fv)$_2$ antibodies, Fab fragments, F(ab')$_2$ fragments, or tandem bodies. Antibodies may be produced according to any suitable method known to the person skilled in the art. Polyclonal antibodies may e.g. be produced by immunization of animals with the antigen of choice, whereas monoclonal antibodies of defined specificity may e.g. be produced using the hybridoma technology developed by Köhler and Milstein. It is noted that an antibody as used herein may also be functionally linked, e.g. comprise a detectable label. The term "binding fragment thereof" relates to a fragment of an antibody, wherein such a fragment is still capable of binding the antigen. Preferably, such a fragment thus still comprises the CDR-regions of the underlying antibody.

The term "peptide" refers to a molecular chain of amino acids connected via peptide bonds. Polypeptides according to the definition may be synthetic polypeptides that may include naturally or non-naturally occurring amino acids. A "fragment" of a peptide lacks at least one amino acid of the given sequence of a peptide.

The term "treatment of AD" or "treating AD" as used herein may also relate to an alleviation of said disease and includes the treatment or alleviation of symptoms of AD.

The term "compound" as used herein relates to any molecule, the skilled person considers suitable for possibly achieving an effect in an assay system comprising a compromised mitochondrial PreP. Particularly, molecules potentially influencing enzymatic activities of mitochondrial proteins will be considered by the skilled person.

The term "assay system" as used herein relates to a typical system used by the skilled person in screening assays. Thus, the assay system may be a fully reconstituted in vitro system, wherein all necessary components are provided in a suitable buffer. The system may also be only partly reconstituted and e.g. comprise specific recombinantly expressed proteins together with isolated mitochondria or mitochondrial extracts gained from in vitro cultured cells, such as mammalian cells or yeast cells. The assays system may also be a system employing living cells, such as e.g. mammalian cells or yeast cells. Exemplary assays are set forth in the example section of the present application. Finally, specific labels such as e.g. fluorescent labels or radioactive labels may be used in the assay system, e.g. to determine the amounts of proteins.

The term "compromised" as used herein relates to an at least partly inactive enzyme, in the present case PreP, which results in an accumulation of at least one premature mitochondrial protein. It is understood that the term "PreP" is used when referring to the human enzyme—if e.g. yeast cells are used, the corresponding yeast homolog (Cym1) is compromised such that at least one premature mitochondrial protein accumulates.

The term "reactive oxygen species" or "ROS" relates to chemically reactive molecules containing oxygen, which increase if mitochondria are compromised. Therefore, ROS can inter alia indicate the condition of mitochondria in cells.

The term "small molecule" as used herein refers to a small organic compound having a low molecular weight. A small molecule may be a synthetic compound not known to occur in nature or a naturally-occurring compound isolated from or known to occur in natural sources, such as e.g. cells, plants, fungi, animals and the like. A small molecule in the context of the present invention preferably has a molecular weight of less than 5000 Dalton, more preferably of less than 4000 Dalton, more preferably less than 3000 Dalton, more preferably less than 2000 Dalton or even more preferably less than 1000 Dalton. In a particularly preferred embodiment a small molecule in the context of the present invention has a molecular weight of less than 800 Dalton. In another preferred embodiment, a small molecule in the context of the present invention has a molecular weight of 50 to 3000 Dalton, preferably of 100 to 2000 Dalton, more preferably of 100 to 1500 Dalton and even more preferably of 100 to 1000 Dalton. Most preferably, a small molecule in the context of the present invention has a molecular weight of 100 to 800 Dalton. It is further preferred that a small molecule in the context of the present invention meets the "Rule of Five" as set out below and is thus orally active (i.e. has a good oral bioavailability); these rules are as follows: the small molecule has no more than five hydrogen bond donors (e.g. nitrogen or oxygen atoms with one or more hydrogen atoms); the small molecule has not more than ten hydrogen bond acceptors (e.g. nitrogen or oxygen atoms); the small molecule has a molecular mass of less than 500 Dalton; the small molecule has an octanol-water partition coefficient log P not greater than 5.

2. Detailed Description of Certain Aspects of the Present Invention

2.1. Underlying Finding Derived from Results Shown in the Example Section

The present invention is based on the surprising finding that the mitochondrial protease MPP (which is responsible for cleavage of N-terminal import presequences from nuclear-encoded mitochondrial proteins (21)) is functionally coupled to the protease PreP (which is responsible for degradation of the N-terminal import presequences).

This functional link has the following implications for AD: It is known that the amyloid beta (Aβ) protein is present in patients suffering from AD and that Aβ is inter alia targeted to mitochondria within cells; further, it is known that Aβ slows down/inhibits the activity of PreP (17). The functional link as found by the inventors results therein that MPP is also slowed down/inhibited. As a consequence, mitochondrial precursor proteins (still comprising N-terminal import presequences) and intermediate mitochondrial precursor proteins (still comprising parts of the N-terminal import presequences) accumulate. In consequence, mitochondrial functions are strongly impaired, e.g. with respect to respiration and the oxidative stress response. As regards the above-mentioned intermediate mitochondrial precursor proteins, it is noted that MPP not only catalyzes the complete cleavage of import presequences (resulting in the mature protein) but in some cases also only cleaves part of the import presequences (resulting in intermediate precursor proteins). Generally, such intermediate precursor proteins are further processed by Oct1/MIP (the octapeptidyl peptidase), which is also slowed down/inhibited if PreP is slowed down/inhibited.

It is noted that mitochondrial dysfunctions including impaired cellular respiration, oxidative stress response, ATP synthesis, mtDNA maintenance and gene expression have been observed at early stages of AD and it has been proposed that mitochondrial dysfunction may serve as peripheral marker for the detection of AD in blood cells, especially in lymphocytes. It has also been proposed that early impairments of mitochondrial dysfunction and oxidative stress may precede Aβ overproduction and deposition (so called "mitochondrial cascade hypothesis"). However, this has not yet been linked to an accumulation of mitochondrial precursor and intermediate precursor proteins.

Due to the link found by the inventors, increased amounts of mitochondrial precursor and intermediate precursor proteins are indicative of the presence and/or an increased amount of Aβ in mitochondria and cells, respectively. Increasing amounts of mitochondrial precursor and intermediate precursor proteins are therefore characteristic for AD and particularly for the early stage of AD.

2.2. Processing of Samples

It can be preferred to process the sample provided in step a) of a method of the first aspect of the present invention prior to carrying out any further step(s).

The processing step(s) inter alia depend on the method to be used for the determination of the amount carried out in step b) (including the determination of the presence/absence of at least one premature mitochondrial protein). Thus, if e.g. a Western-blot is used as immunological method, the final sample to be analyzed is typically provided in a denaturing buffer. For MS-analysis, different buffers known to the skilled person are available and are used in accordance with routine proceedings. Exemplary preparations, buffers and the like depending on the method to be used are given in the example section of the present application.

Further, the processing step(s) also depend on the sample used in the method. If a tissue sample and in particular a brain sample (e.g. a sample from the temporal cortex) is used, the tissue is typically homogenized in order to lyse cells; a next step may be a centrifugation or the like to remove unbroken cells and nuclei. Typically, the mitochondria are then collected from the lysate by another centrifugation and lysed using e.g. a suitable lysis buffer. The protein content of this mitochondrial lysate is then typically analyzed in the subsequent step, wherein common methods such as determination of the concentration etc. may be used for standardization reasons. An exemplary processing of human brain samples is given in the example section of the present application.

If blood as body fluid is used as sample, it may be necessary to concentrate mitochondria-containing cells; thus, the separation of erythrocytes can be preferred in order to remove cells, which do not contain any mitochondria—standard procedures known to the skilled person may be used for the separation of erythrocytes. It can therefore be preferred to collect and concentrate leukocytes and thrombocytes, followed by a lysis of said cells according to standard methods. The mitochondria may then be collected and lysed. The cells may also be directly used. As noted above for a brain sample, the protein content of the mitochondrial lysate is then typically analyzed in the subsequent step, wherein common methods such as determination of the concentration etc. may be used for standardization reasons. However, one may also use the supernatant of a body fluid sample (in particular blood) directly after an initial centrifugation step or even the body fluid sample itself, wherein a concentration step of the supernatant and sample, respectively (optionally carried out by ultrafiltration) might be required in order to concentrate the mitochondrial preproteins to be detected. It is noted that Example 3.3 below describes an exemplary way of using blood as sample.

If skin is used as sample, it is preferred to use the fibroblasts comprised therein as cells underlying the analysis. In order obtain a sufficient quantity of fibroblasts from a skin sample, it may be necessary to isolate the fibroblasts and/or concentrate the fibroblasts. It is preferred to cultivate the fibroblasts according to standard methods prior to carrying out the analysis in order to increase the fibroblast cell number. The use of skin fibroblasts and such standard methods have been described earlier, e.g. in WO 02/067764 (see in particular the section "Processing and culture of fibroblasts from fresh biopsies on pages 22 and 23 of WO 02/067764).

Typical protocols and buffers are known to the skilled person and can e.g. be found on the following two homepages: embl.de/pepcore/pepcore_services/protein_purification/extraction_clarification/lysis_buffer_additives/en.wikipedia.org/wiki/Lysis_buffer Thus, a method of the present invention including the above mentioned additional steps may also be formulated as follows:

Method of diagnosing Alzheimer's disease (AD) in a patient comprising the following steps:
Providing a sample from a patient potentially suffering from AD;
Collecting and/or concentration cells containing mitochondria from said sample;
Lysing said cells and optionally collecting and/or concentrating mitochondria;
Lysing said cells/mitochondria;
Determining the amount of at least one premature mitochondrial protein, wherein said premature mitochondrial protein comprises at least part of its mitochondrium-targeting presequence; and
Comparing the amount obtained in the previous step to the amount of said at least one premature mitochondrial protein determined in a control sample, wherein said control sample is derived from a subject not suffering from AD;
wherein a higher amount of said at least one premature mitochondrial protein in the sample from a patient potentially suffering from AD compared to the amount of said at least one premature mitochondrial protein in the control sample indicates AD in said patient.

2.3. Preferred Precursor Proteins

Precursor and intermediate precursor forms of the following mitochondrial proteins are particularly preferred in the present invention (wherein all isoforms and splice variants are also included); in the following, not only details about these proteins but also their mitochondrium-targeting presequences will be given (starting from the N-terminus):

```
hMdh2: Human malat dehydrogenase 2, mitochondrial
[MDH2 human, GenBank acc. no. CAG38785.1]
                                    (SEQ ID No.: 20)
MLSALARPASAALRRSFSTSAQNN hOAT: Human ornithin aminotransferase,
mitochondrial
[OAT human, UniProtKB acc. no. P04181]
                                    (SEQ ID No.: 21)
MFSKLAHLQRFAVLSRGVHSSVASATSVATKKTVQ hACADV: Human very long-chain specific acyl-CoA
dehydrogenase, mitochondrial
[ACADV human, UniProtKB acc. no. P49748]
                                    (SEQ ID No.: 22)
MQAARMAASLGRQLLRLGGGSSRLTALLGQPRPGPARRPY PMPCA: mitochondrial-processing peptidase subunit
alpha, mitochondrial
[UniProtKB acc. no. Q10713]
                                    (SEQ ID No.: 23)
MAAVVLAATRLLRGSGSWGCSRLRFGPPAYRRF CLYBL: Citrate lyase subunit beta-like protein,
mitochondrial
[UniProtKB acc. no. Q8N0X4]
                                    (SEQ ID No.: 24)
MALRLLRRAARGAAAAALLRLK PPM1K: Protein ph, mitochondrial
[PPM1K, UniProtKB acc. no. Q8N3J5]
                                    (SEQ ID No.: 25)
MSTAALITLVRSGGNQVRRRVLLSSRLLQ SLIRP: Stem-loop-interacting RNA-binding protein,
mitochondrial
[SRA, UniProtKB acc. no. Q9GZT3]
                                    (SEQ ID No.: 26)
MAASAARGAAALRRSINQPVAFVRRIPW NDUFA9: NADH dehydrogenase [ubiquinone] 1 alpha
subcomplex subunit 9, mitochondrial
[NDUA_human, UniProtKB acc. no. Q16795]
                                    (SEQ ID No.: 69)
MAAAAQSRVVRVLSMSRSAITAIATSVCHGPPCRQ MRPL23: 39S ribosomal protein L23, mitochondrial
[RM23_human, UniProtKB acc. no. Q16540]
                                    (SEQ ID No.: 70)
MARNVVYPLYRLGGPQLRVFRT
```

3. Examples

3.1. Example 1

Mitochondrial dysfunction plays an important role in the pathology of Alzheimer's disease (AD). Although it is still unclear if mitochondrial dysfunction is cause or consequence of AD and how it is connected to other cellular dysfunctions (1-4), Aβ appears to accumulate in mitochondria of AD patients and affects a multitude of functions including respiration, detoxification of reactive oxygen species (ROS) and organellar morphology (2, 5-14). Aβ can be cleared by the mitochondrial matrix peptidasome PreP, a metallopeptidase that degrades peptides including presequence peptides generated upon maturation of imported precursor proteins and that has a decreased activity in AD (15-17). Many mitochondrial proteins contain N-terminal presequences that direct these precursors from the cytosol into the organelle. Upon import, presequences are cleaved by the mitochondrial processing peptidase MPP in the matrix releasing the mature protein (18-21). In several cases MPP generates intermediate forms that are further processed by the octapeptidyl peptidase Oct1/MIP or the intermediate cleaving peptidase Icp55.

Isolated mitochondria from post mortem brain samples of four AD patients and four age-matched non-AD controls (table S2) were analyzed and the presence of higher molecular precursor species of the matrix protein MDH2 in all patient samples but not in controls was observed (FIG. 1A). Similar observations, i.e. the detection of higher molecular precursor species, were made for the proteins NDUFA9 and MRPL23 (data not shown). An antibody raised against the presequence peptide of MDH2 that recognizes only precursor but not the mature cleaved protein confirmed specific accumulation of the MDH2 precursors in AD mitochondria (FIG. 1B). It was speculated that Aβ accumulation delays matrix peptide turnover and thereby induce feedback inhibition of presequence processing enzymes.

Figure 5:
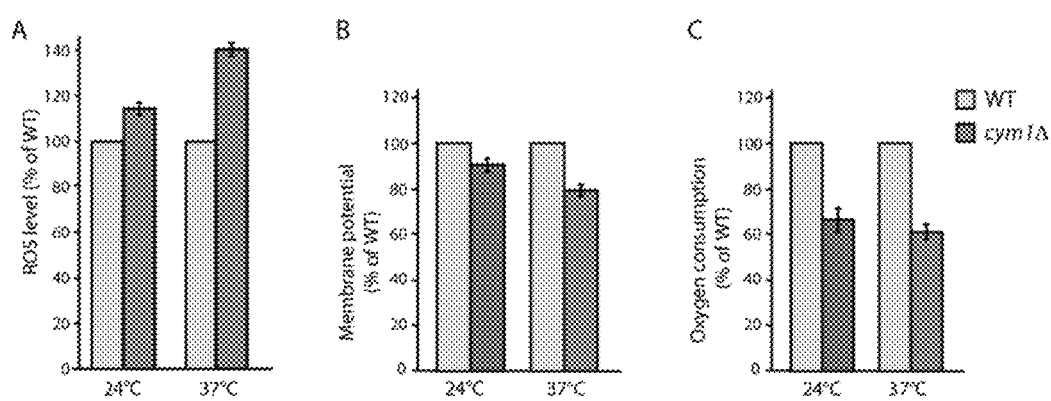
FIG. 5. Analysis of ROS levels, membrane potential and O$_2$ consumption (as described in supplementary materials) in wild-type (WT) and cym1ΔS, mitochondria isolated from yeast strains grown at 24° C. or with an additional in vivo shift to 37° C. for 6 h (in YPG). WT was set to 100%, mean±SEM (n=3).

To uncover a functional link between mitochondrial preprotein maturation and peptide turnover and its potential role in Aβ toxicity, S. cerevisiae that represents an ideal model organism to study basic mechanisms underlying human diseases including AD was used (3, 25). A mutant was generated that lacks the yeast PreP homolog Cym1 (26) and harbors a temperature-sensitive allele of the essential MPP subunit Mas1 (18, 19, 21). The mutant was not able to grow under respiratory conditions (i.e. conditions in which mitochondrial energy metabolism is essential for cell viability) indicating a genetic interaction of the presequence peptidase MPP and the peptidasome Cym1 (FIG. 1C). To test if impaired peptide degradation affects the presequence processing activity of MPP, a global mass spectrometric analysis of mitochondrial N-termini in cym1Δ mitochondria using COFRADIC (combined fractional diagonal chromatography) (21) was performed and a large number of N-termini in cym1Δ mitochondria corresponded to non-processed precursors or processing intermediates of dually processed proteins when compared to the N-proteome of wild-type mitochondria (21). Western blot analysis of several mitochondrial proteins revealed a strong accumulation of precursor forms, processing intermediates and decreased levels of cleaved, mature proteins in cym1Δ mitochondria in comparison to wild-type (FIGS. 1D and E). Affected proteins encompass a variety of mitochondrial functions including respiration, ATP synthesis, mtDNA maintenance and gene expression or oxidative stress response (FIGS. 1D and E). Analysis of cym1 mutants that lack critical residues of its metal binding motif (HXXEH) (26) indicated that accumulation of precursor proteins depended on Cym1 protease activity (FIG. 1F). Testing of various mitochondrial functions in cym1Δ mitochondria revealed increased levels of ROS, decreased membrane potential and impaired $O_2$-consumption compared to wild-type (FIG. 5). Similar effects have been observed in AD mitochondria (2, 6, 7, 10, 17).

Figure 2:
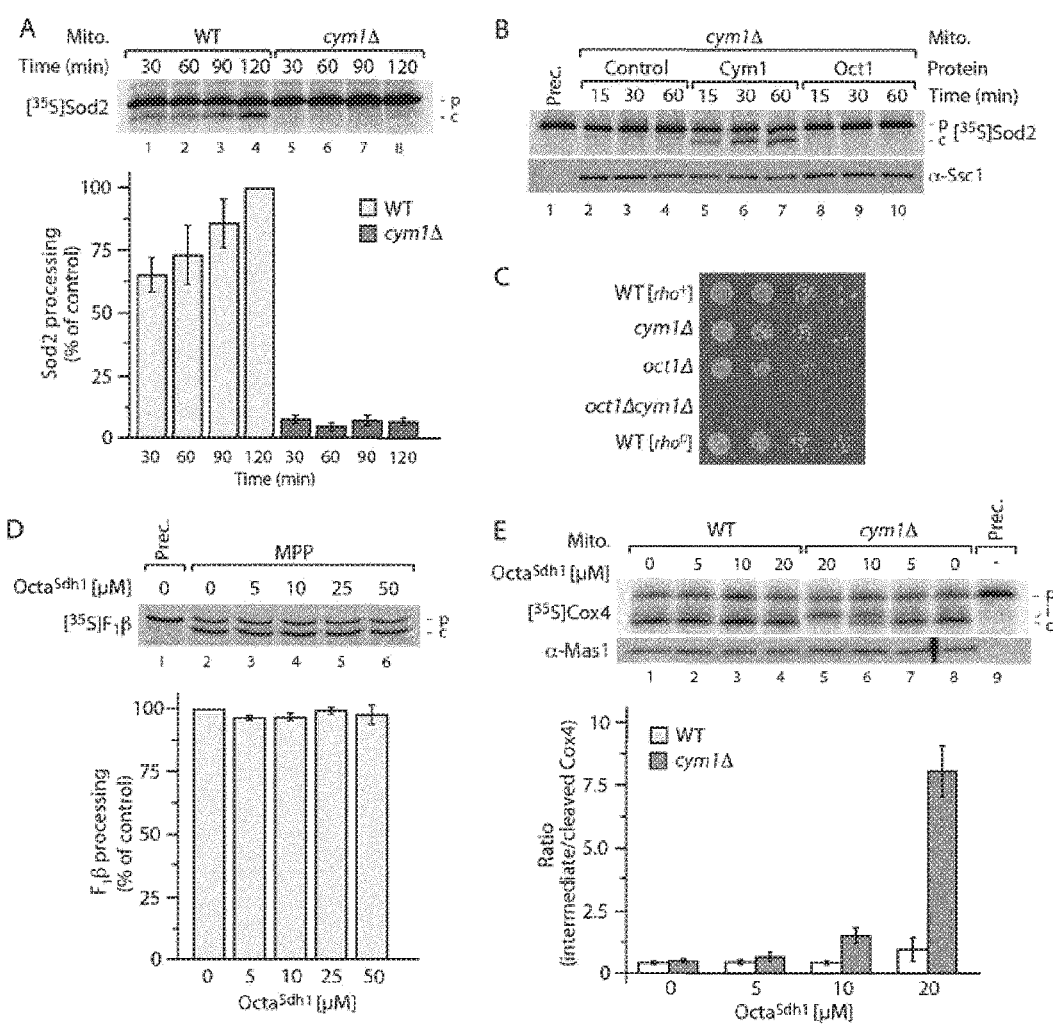
FIG. 2. Mitochondrial precursor maturation depends on efficient peptide turnover. (A) In vitro processing of [$^{35}$S]Sod2 precursor in soluble extracts of wild-type (WT) and cym1Δ mitochondria in the presence of 10 μM Cox4 presequence peptide. (B) In vitro synthesized Cym1 protein restores Sod2 precursor processing in cym1Δ mitochondrial extract. Control, wheat germ lysate. (C) Synthetic growth defect of cym1Δoct1Δ double mutant yeast strain (23° C., YPD). (D) Processing of [$^{35}$S]F$_1$β precursor by purified MPP is not inhibited by octapeptides. (E) In vitro processing assay of [$^{35}$S]Cox4 precursor in WT and cym1Δ mitochondrial extract in the presence of octapeptides. Quantifications represent mean±SEM (n=4 for (A) and (E); n=3 for (D)).
Figure 6:
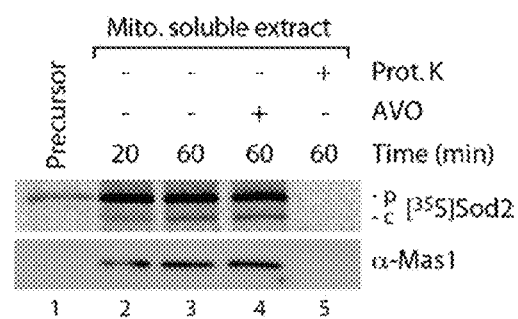
FIG. 6. In vitro processing of a mitochondrial precursor protein in soluble mitochondrial extracts. [$^{35}$S]Sod2 precursor was incubated with soluble WT mitochondrial extract for indicated periods. Samples were separated by SDS-PAGE and radiolabelled proteins were detected by phosphoimaging. In contrast to in organello import (39) precursor processing in vitro does not depend on addition of AVO that dissipates the membrane potential ΔΨ and the cleaved protein is not protected to Proteinase K (Prot. K) treatment. p, precursor; c, cleaved protein. Mas1, loading control.
Figure 7:
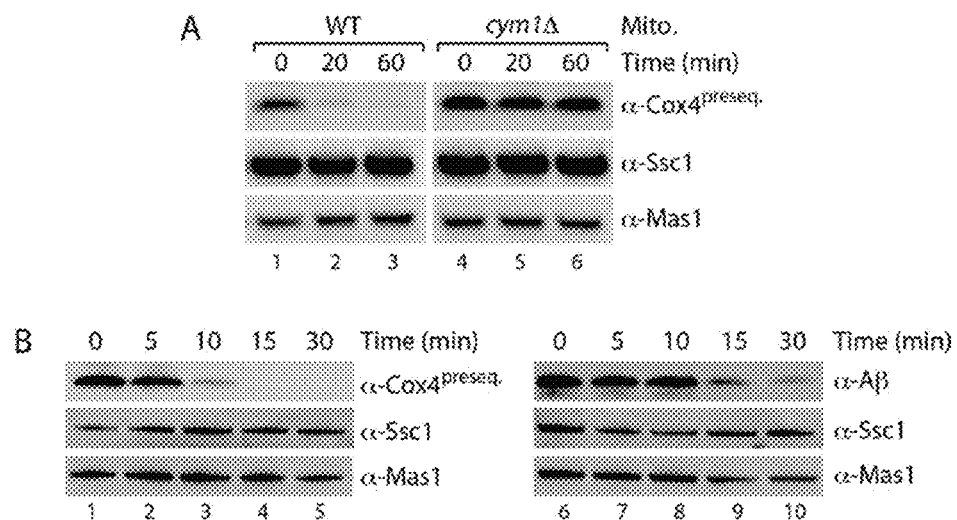
FIG. 7. Peptide degradation assay in soluble mitochondrial extracts. (A) Rapid degradation of Cox4 presequence peptide (10 μM) in wild-type (WT) mitochondrial extract. Degradation is inhibited in cym1Δ samples. (B) Delayed degradation of Aβ peptide (10 μM) compared to Cox4 presequence peptide (10 μM) in wild-type mitochondrial extract. Ssc1 and Mas1, loading controls.
Figure 8:
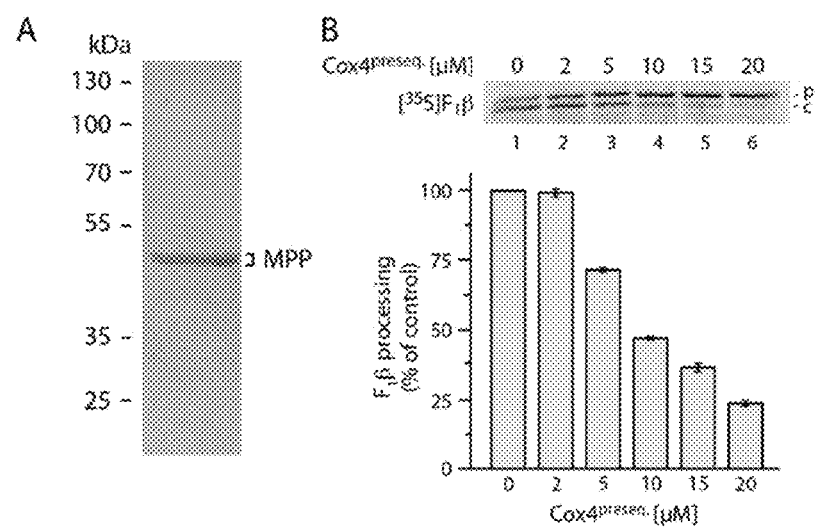
FIG. 8. In vitro processing assay with purified MPP. (A) Tandem-purified MPP subunits Mas1 and Mas2 were separated via SDS-PAGE. Gel was stained with coomassie brilliant blue. (B) Processing activity of radiolabelled F$_1$β precursor by purified MPP is inhibited by increasing concentrations of Cox4 presequence peptide (19). Processed F$_1$β was analyzed by autoradiography after SDS-PAGE and quantified by Multi Gauge software. Error bars represent SEM of three independent experiments.

To directly analyze a dependence of preprotein maturation on peptide turnover an in vitro processing assay was employed in mitochondrial extracts (FIG. 6) (16) from wild-type and cym1Δ mitochondria. Presequence peptides were rapidly degraded in wild-type but not cym1Δ extracts (FIGS. 7A and B). In the presence of a typical presequence peptide ($Cox4^{preseq.}$) (19) the in vitro processing of radiolabelled Sod2 precursor by MPP was efficiently blocked in the absence of Cym1 (FIG. 2A). Cox4 presequence peptides were able to inhibit purified MPP in similar concentrations (FIG. 8) (19). Upon addition of cell-free translated Cym1 protein the MPP processing activity could be restored in cym1Δ extracts (FIG. 2B). These results suggest that impaired turnover of presequence peptides leads to inhibition of MPP activity explaining the precursor accumulation in cym1Δ mutant mitochondria in vivo (FIGS. 1D and E). However, it was puzzling why also precursor processing intermediates accumulated in the cym1Δ mutant (FIG. 1D). It has been proposed that PreP/Cym1 requires a minimal substrate length of 11 amino acids while the intermediate peptidase Oct1 generates octapeptides (15, 23). An oct1Δcym1Δ double mutant was generated and the observed synthetic growth defect pointed to a functional link between both enzymes (FIG. 2C). It was found that MPP processing activity was not affected by octapeptides (derived from the Oct1 substrate Sdh1) in contrast to presequence peptides (FIG. 2D and FIG. 8). However, in vitro processing of the Cox4 precursor that is cleaved sequentially by MPP and Oct1 revealed a specific impairment of the Oct1-dependent processing step in cym1Δ in the presence of octapeptides (FIG. 2E). This indicated that Cym1 also degrades shorter peptides and that an impaired turnover of MPP generated presequences and Oct1 derived octapeptides leads to an inhibition of presequence processing enzymes causing accumulation of precursors and processing intermediates. Impaired maturation might lead to decreased stability of mitochondrial proteins (19, 21-24) and reduced amounts of mature proteins (FIGS. 1D and E).

Figure 3:
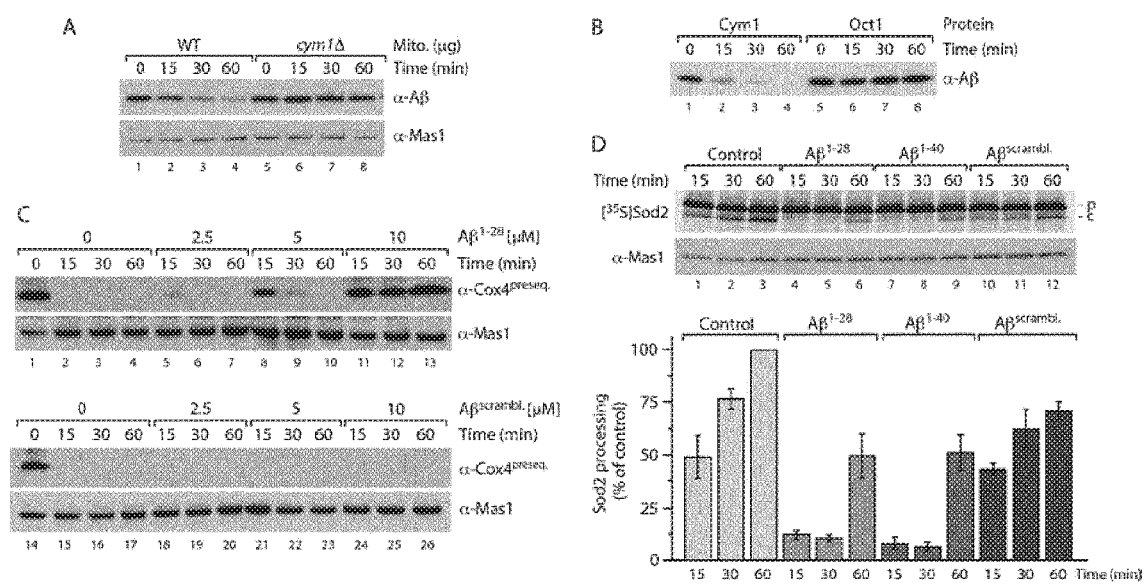
FIG. 3. Aβ impairs mitochondrial peptide turnover leading to feedback inhibition of presequence processing enzymes. (A) Aβ degradation in soluble extracts of wild-type (WT) and cym1Δ mitochondria. (B) Aβ degradation by cell free translated Cym1 (wheat germ lysate). Oct1, Oct1 translated in wheat germ lysate. (C) Aβ$^{1-28}$ but not Aβ$^{scrambled}$ peptide impairs Cox4 presequence peptide degradation in WT soluble mitochondrial extract. 10 μM Cox4 presequence peptide was added in each reaction. Mas1, loading control. (D) In vitro processing of [$^{35}$S]Sod2 precursor in WT mitochondrial extract in the presence of indicated Aβ peptides (10 μM) and 10 μM Cox4 presequence peptide. Control 60 min was set to 100%, mean±SEM (n=3).
Figure 9:
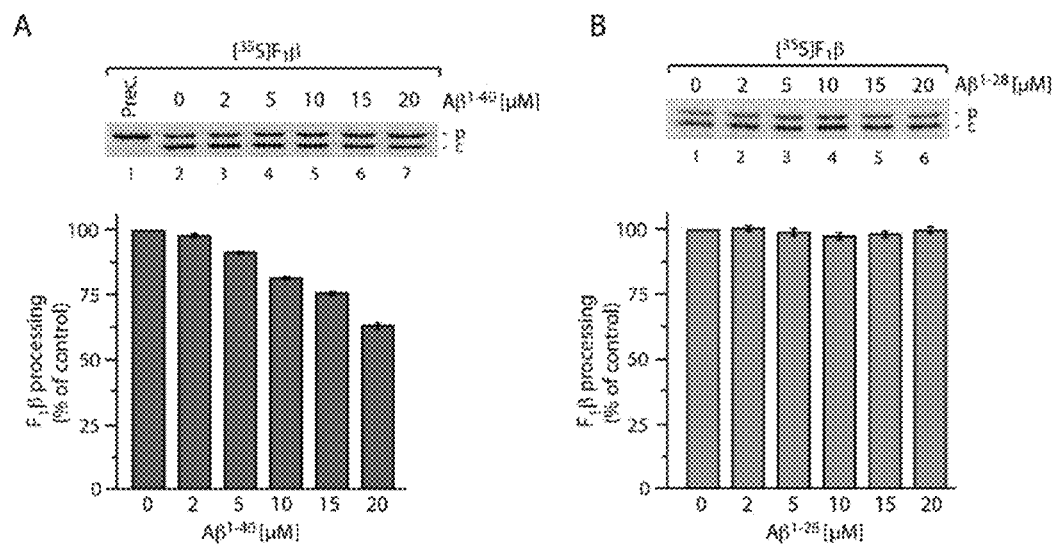
FIG. 9. In vitro processing assay of radiolabelled F$_1$β precursor by purified MPP in the presence of increasing concentrations of Aβ$^{1-40}$ (A) or Aβ$^{1-28}$ (B) peptides. Reactions were performed as described in FIG. 8B. Error bars represent SEM of three independent experiments.

It was found that Aβ peptides were degraded by Cym1 in mitochondrial extracts and by the recombinant enzyme (FIGS. 3A and B). However, degradation of Aβ was slower compared to turnover of presequence peptides (FIG. 7B). Presence of Aβ but not of a scrambled form appeared to impair presequence degradation capacity of Cym1 (FIG. 3C). When MPP activity in the presence of Aβ was tested a striking delay in precursor processing of Sod2 was found (FIG. 3D). It was noticed that $Aβ^{1-40}$ (unlike the shorter version $Aβ^{1-28}$) slightly inhibited activity of purified MPP at higher concentrations (FIG. 9) and therefore the shorter version was included in the functional assays.

Figure 4:
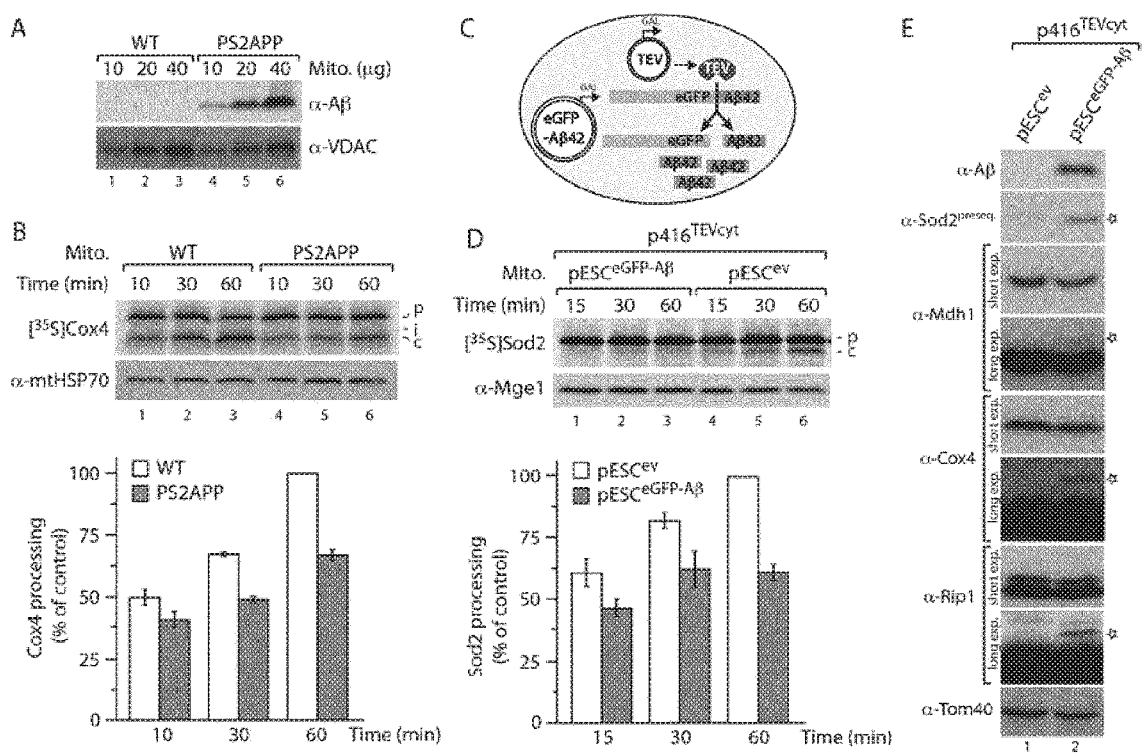
FIG. 4. Mitochondrial Aβ inhibits precursor maturation. (A) Immunoblot analysis of purified mitochondria from wild-type (WT) and PS2APP mouse brain tissue (from 12 month old mice) reveals presence of Aβ in PS2APP mitochondria. (B) In vitro processing assay of Cox4 precursor in WT and PS2APP mouse brain mitochondrial extract. mtHSP70, loading control. Quantifications represent mean±SEM (n=3). (C) Inducible expression system for generation of free Aβ$^{1-42}$ peptide in the cytosol. (D) In vitro processing assay of [$^{35}$S]Sod2 precursor in yeast mitochondrial extracts isolated from coa6Δ strains harbouring empty vector pESC$^{ev}$ or pESC$^{eGFP-Aβ}$ (1d induction on galactose medium). Both strains coexpressed TEV protease (p416$^{TEVcyt}$). Quantifications represent mean±SEM (n=3). (E) Immunoblot analysis of purified mitochondria from strains described in (D) after 3d induction on galactose medium. exp., exposure time. Stars indicate accumulating precursor proteins.
Figure 10:
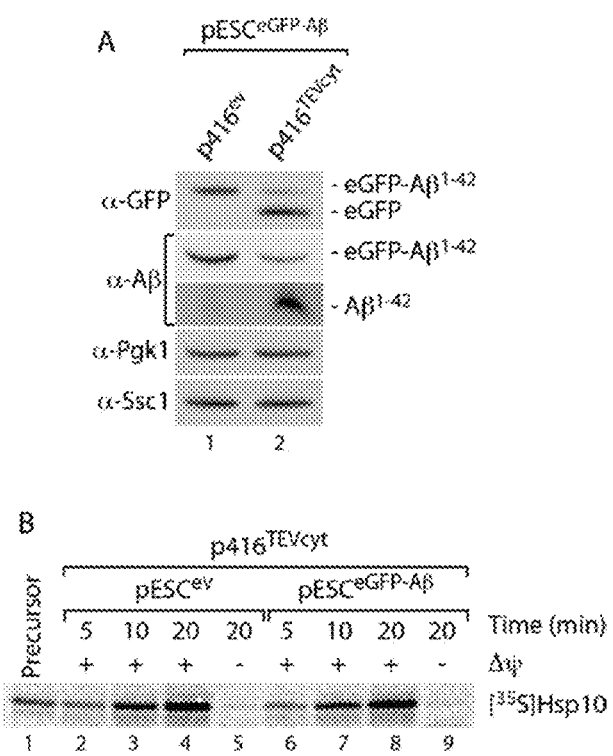
FIG. 10. In vivo yeast model that generates free Aβ$^{1-42}$ in the cytosol. (A) Wild-type yeast strain expressing an eGFP-TCS-Aβ$^{1-42}$ fusion protein after 1 d shift to galactose containing medium (30° C.). Whole yeast cell extract was loaded on SDS-PAGE and immunodecoration was performed with indicated antibodies. Coexpression of cytosolic TEV protease (TEV$^{Cyt}$) by the p416$^{TEVcyt}$ vector led to the generation of Aβ$^{1-42}$. p416$^{ev}$, coexpression of empty vector. TCS, TEV cleavage site; Pgk1, Phosphoglycerol kinase as cytosolic marker; Ssc1, mitochondrial Hsp70. (B) Mitochondrial presequence import pathway is not impaired upon Aβ expression. [$^{35}$S]Hsp10 precursor that contains no cleavable presequence was imported into coa6Δ mitochondria that expressed free Aβ$^{1-42}$ (lanes 6-9) or the empty vector (lanes 2-5). Samples were treated with Proteinase K and membrane potential (ΔΨ) was dissipated by addition of AVO prior to the import reaction where indicated (39).
Figure 11:
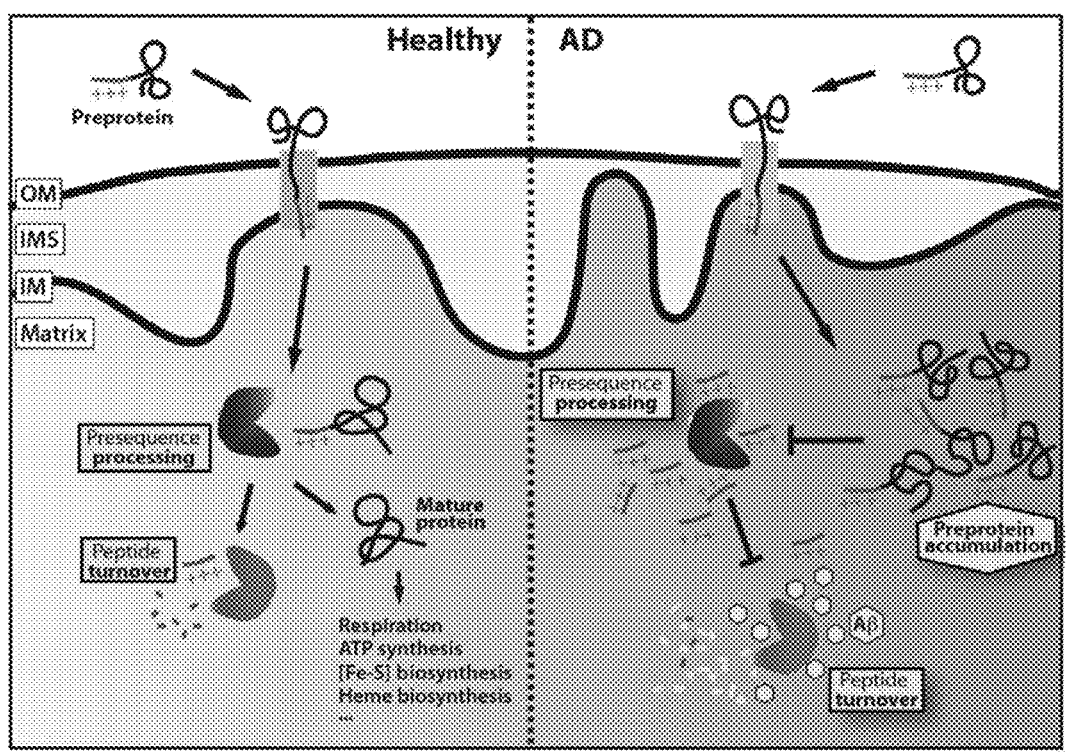
FIG. 11. Model of Aβ induced inhibition of mitochondrial preprotein maturation. In healthy cells (left panel) mitochondrial preproteins are imported from the cytosol and presequences are efficiently cleaved off by presequence processing enzymes. Presequence peptides (shown in red) are then degraded by the peptidasome PreP, that constitutes the mitochondrial peptide turnover machinery. Peptide turnover is impaired in the presence of Aβ (AD, right panel) leading to inhibition of presequence processing and accumulation of preproteins.
Figure 12:
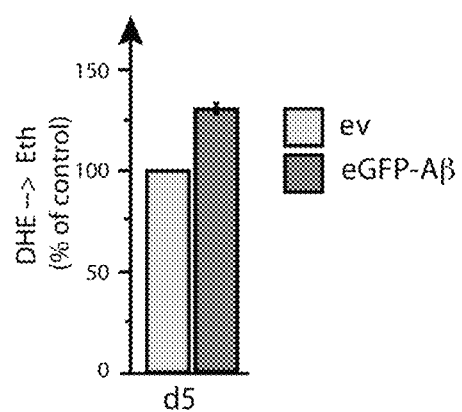
FIG. 12. Analysis of ROS levels in empty vector control (ev) and Abeta42 (eGFP-Aβ) mitochondria isolated from yeast strains grown at 30° C. for 5 days (in minimal medium w/o histidine w/o uracil containing galactose as carbon source). Empty vector control was set to 100%, mean±SEM (n=9).

The next question was if mitochondrial Aβ could impair precursor maturation and two model systems were chosen. Firstly, freshly prepared soluble extracts from brain mitochondria of PS2APP mice were tested. This AD model harbors mutations in the PS2 (N141I) and APP (Swedish FAD) genes and shows Aβ accumulation in mitochondria (FIG. 4A) (10, 27). Indeed, processing of the Cox4 precursor was significantly impaired in PS2APP samples compared to age-matched wild-type mice (FIG. 4B). Secondly, a yeast model was established that allowed galactose-induced expression of an eGFP-Aβ$^{1-42}$ fusion protein that harbors a cleavage site for TEV protease (FIG. 4C). Coexpression of TEV protease led to release of Aβ peptides in the cytosol (FIG. 10A). To mimic an aging-related mitochondrial dysfunction we used the coa6Δ strain that showed a moderate instability of respiratory chain complexes (28, 29) and induced eGFP-Aβ$^{1-42}$ expression by 1 d incubation on galactose. Aβ localized to mitochondria and impaired maturation of Sod2 precursor in soluble mitochondrial extracts (FIGS. 4D and E). The presequence import pathway was not compromised by Aβ (FIG. 10B). After 3d induction we observed in vivo accumulation of several mitochondrial precursor proteins in the Aβ-expressing strain (FIG. 4E). Based on the data, the model shown in FIG. 11 can be proposed.

3.2. Example 2

The aim of this example was to detect and determine human mitochondrial proteins comprising at least part of their N-terminal presequence (i.e. preproteins) in brain samples from AD patients compared to age-matched controls without AD.

The samples were analyzed according to the CHAFRADIC method described in Venne et al., J. Proteome Res. 12, 3823 (2013). Human mitochondrial samples (see section 3.3. below for details) were lysed with lysis buffer (2% SDS, 150 mM NaCl, 50 mM Tris, pH 7.8) and subsequently carbamido-methylated. Thus, the lysates were initially reduced with 10 mM DTT for 30 minutes at 56° C. and then alkylated with 20 mM IAA for 30 minutes at room temperature in the dark.

For the specific dimethyl-labeling of the free protein N-termini and lysine-residues, 100 µg of each of the control and AD-sample were treated with a light and heavy labeling, respectively, for 2 hours at 37° C. according to the protocol by Jentoft et al., J Biol Chem 1979, 254(11):4359-4365. For conducting the light labeling, the control sample was incubated with 20 mM CH$_2$O, 40 mM NaBH$_3$CN in 200 mM HEPES, pH 8.0. The AD sample was labeled with a heavy label by using 20 mM CD$_2$O, 40 mM NaBD$_3$CN in 200 mM HEPES. The reaction was blocked via incubation with 60 mM glycine for 10 minutes and 130 mM hydroxylamine for 15 minutes at room temperature. The samples were then pooled in a ratio of 1:1 and an ethanol precipitation was carried out.

The pooled sample was treated with ice-cold ethanol in a ratio of 1:10 and incubated for 1 hour at −40° C., followed by pelleting the proteins via centrifugation at 4° C. for 30 minutes. After discharging the supernatant, the pellet was dried initially at room temperature and then solubilized in 40 µL 2M GuHCl, 50 mM Na$_2$HPO$_4$, pH 7.8. The protein solution was then diluted for the subsequent proteolytic digestion with digestion buffer (50 mM NH$_4$HCO$_3$, 5% Acetonitril, 1 mM CaCl$_2$, pH 7.8) in a ratio of 1:10. The proteolytic digestion was carried out using trypsin from Promega in a ratio of 1:30 for 12 hours at 37° C.

After a monolithic digestion control was carried out (Burkhart J M et al-. J Proteomics 2012; 75(4):1454-1462), the sample was prepared for the strong cation exchange, SCX. The sample was desaltet using a 4 mg C18 SPEC cartridge. SCX separation was carried out on a U3000 HPLC system (Thermo Scientific) in combination with a 150×1 mm POLYSULFOETHYL A column (PolyLC, Columbia, US, 5 µm particle diameter, 200 A pore size) using three buffers: SCX buffer A (10 mM KH$_2$PO$_4$, 20% ACN, pH 2.7), SCX buffer B (10 mM KH$_2$PO4, 188 KCl, 20% ACN, pH 2.7) and SCX buffer C (10 mM KH$_2$PO$_4$, 800 mM NaCl, 20% ACN, pH 2.7). 100 µg of the desalted sample were resuspended in 50 µl SCX buffer A and separated at a flow of 80 µg/ml with a gradient optimized for the peptide charge conditions: over 10 minutes, 100% SCX buffer A was used; then, the ratio of SCX buffer B increased over 18 minutes from 0 to 20%, wherein the gradient was maintained for 10 minutes at 20% SCX buffer B. Then, the ratio of SCX buffer B was increased within 2 minutes in a linear way to 40% B and maintained for further 5 minutes, before the ratio of SCX buffer B was increased in a linear way within 5 minutes to 100%. After 5 minutes at 100% SCX buffer B, the column was washed for 5 minutes with 100% SCX buffer C. Fractions of the charge conditions +1, +2, +3, +4, +5 were automatically collected and concentrated to a volume of 40 µl employing vacuum.

For chemical derivatization of the N-termini of internal peptides, the fractions were adjusted to a final volume of 300 µl with 200 mM Na$_2$HPO$_4$, pH 8.0 and then in two steps incubated for 1 hour each with initially 20 mM and then 10 mM NHS-trisdeuteroacetate at 37° C. (Staes A et al., Nat Protoc 2011, 6(8):1130-1141). The reaction was blocked via incubation with 60 mM glycine for 10 minutes and 130 mM hydroxylamine for 15 minutes at room temperature. The fractions were then desalted as described above using 4 mg C18 SPEC cartridges (Agilent) and after concentrating the samples to the dry state dissolved in 50 µl SCX buffer A. Rechromatography of the charge conditions+1, +2, +3, +4, +5 took place under the conditions described above in independent separations, wherein again the corresponding charge conditions were collected. They were then desalted as described above using 4 mg C18 SPEC cartiladges (Agilent) and after concentration to the dry sate resuspended under vacuum in 15 µl 0.1% trifluoroacetic acid (TFA).

The quantitative analysis of the concentrated N-terminal peptides was carried out using LC-MS and the results are given in the following table:

Identification of mitochondrial N-termini of mitochondrial precursor proteins from human brain mitochondria (temporal lobe); peptide ratios are given in AD/controls; grey: accumulated presequence peptides.

3.3. Detection of Premature MDH2 in Blood

| | | | | | | PATIENT 2 | | | PATIENT 1 | | |
|---|---|---|---|---|---|---|---|---|---|---|---|
| | | Pre-sequence | identified N-terminal peptide | | | times quantified (quan) and identified | | median AD/control ratio and corresponding standard deviation | times quantified (quan) and identified | | median AD/control ratio and corresponding standard deviation |
| | | acc. to | First | Last | | (PSMs) | | MD    SD | (PSMs) | | MD    SD |
| Acc. | Protein | Uniprot | AA | AA | Sequ | #quan | #PSMs | ratio   ratio | #quan | #PSMs | ratio   ratio |
| P04181 | OAT_HUMAN Ornithine aminotransferase, mitochondrial | 1 to 36 | 26 | 46 | tSVATk kTVQG PPTSD DIFER | 3 | 7 | 2.31   0.10 | 4 | 8 | 2.87   0.29 |
| P49748 | ACADV_HUMAN Very long-chain specific acyl-CoA dehydrogenase, mitochondrial | 1 to 40 pred. | 7 | 16 | aASLG RQLLR | | | | 11 | 37 | 100.00   36.73 |
| Q10713 | Mitochondrial-processing peptidase subunit alpha | 1 to 33 | 2 | 10 | aAVVL AATR | 1 | 2 | 8.91 | 2 | 6 | 6.76   3.66 |
| Q8NOX4 | Citrate lyase subunit beta-like protein, mitochondrial | 1 to 22 pred. | 9 | 20 | aARGA AAAAL LR | 4 | 5 | 100.00 | | | |
| Q8N3J5 | PPM1K_HUMAN Protein ph | 1 to 29 | 4 | 11 | aALItL VR | 9 | 17 | 100.00 | 4 | 6 | 77.02   26.74 |
| Q9GZT3 | SRA stem-loop-interacting RNA-binding protein, mitochondrial | 1 to 28 pred. | 4 | 13 | sAARG AAALR | 4 | 13 | 100.00 | 1 | 3 | 100.00 |

Fresh blood samples were taken from two patients diagnosed with AD and two age-matched human subjects not suffering from AD (referred to as controls in the following).

Peripheral blood mononuclear cells (PBMCs) were isolated from the samples and cryopreserved according to reference 43. Briefly, PBMC were isolated from fresh EDTA blood, diluted with the same volume of $Ca^{2+}Mg^{2+}$ free Hanks balanced salt solution (HBSS from PAA) or phosphate buffer saline (PBS from PAA) and pipetted carefully over Ficoll-Hypaque (Linaris) gradients in Falcon tubes with 1:2 ratio of Ficoll-Hypaque to diluted blood. After centrifugation (25-30 minutes, 810 g, no brake, room temperature) the interface with the PBMCs was collected. Cells were washed three times with HBSS (10 min, 300 g, room temperature) and counted with a hemocytometer using trypan blue (Sigma) to discriminate between living and dead cells. For freezing, cells were resuspended cautiously with 40% foetal calf serum (FBS from Sigma or FCS from Invitrogen) in RPMI 1640 (Gibco) at room temperature. The same volume of 20% DMSO (Serva) in RPMI was added in two steps with 5 min waiting in between. Cells in special cryovials (Greiner) were placed into cardboard boxes and moved immediately to a −80° C. freezer and to liquid nitrogen for long term storage.

Subsequently, the PBMCs were further fractionated in the "monocytes" and the "non-monocytes" fractions.

In order to separate the PBMCs into these two fractions, the MACS technology by Miltenyi was used. Following the manufacturer's (Miltenyi, Bergisch Gladbach, Germany) instructions, PBMCs were incubated with FC receptor blocker (provided by the manufacturer) to block unspecific antibody binding, washed and incubated with special monoclonal antibodies which target specific surface molecules on the desired cell population (in the present case CD14 for monocyte isolation) or in case of negative selection on the rest of the PBMCs (i.e. non-monocytes). These antibodies are linked to super paramagnetic particles (MACS Micro-Beads). When the cell suspension was pipetted onto columns (provided by the manufacturer) on which a strong magnetic field is applied the labelled cells were retained. Through simple rinsing the non-labelled cells were collected. After detaching the column from the magnet also the labelled cell fraction was rinsed, collected and used for further experiments. With a hemocytometer (Neubauer chamber) the yield of each fraction was checked and the purity and success of the separation was confirmed by flow cytometry according to standard methods.

Following the above procedure, (i) monocytes and (ii) non-monocytes fractions derived from PBMC were available from two AD patients and two controls.

Figure 13:
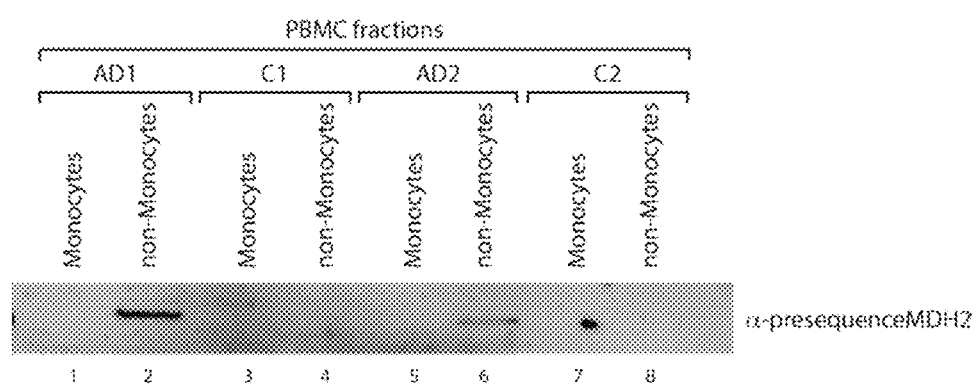
FIG. 13. Mitochondrial precursor proteins accumulate in blood samples from AD patients. Starting from whole blood samples from two AD patients and two controls, PBMCs were isolated and then fractionated in the "monocytes" and "non-monocytes" fractions. The fractions were analyzed for the presence of precursor MDH2 by Western-Blot using a presequence specific antibody. As can be derived from the Western-Blot, precursor MDH2 can be detected in the "non-monocytes" fractions from blood samples derived from AD patients but not in the samples from the controls.

Samples of these fractions were separated by a denaturing SDS-PAGE (a protein amount of about 10 μg was used for each sample [and thus per lane]) according to standard methods, and a Western-Blot was carried out according to standard methods using the afore-mentioned antibody recognizing only precursor MDH2 (but not the mature cleaved protein, see also experimental procedures described in the following example). As can be derived from FIG. 13, MDH2 precursors are present and thus accumulate in the non-monocytes fraction of the blood samples of AD-patients, but not in the controls (note that the "dot"-signal in the monocytes-fraction of C2 in FIG. 13 is an artefact). Accordingly, human mitochondrial proteins comprising at least part of their N-terminal presequence can specifically be detected in blood samples of AD patients.

3.4. Experimental Procedures Used in the Above Examples

Yeast Strains and Growth Conditions

Yeast strains used in this study are listed in table S1. Yeast cells were grown on YPD medium (1% (w/v) yeast extract, 2% (w/v) bacto-peptone, 2% (w/v) glucose) or YPG medium (containing 3% (w/v) glycerol instead of glucose). Deletion mutants were generated by homologous recombination (31). For growth tests yeast cells were cultured in 5 ml YPD medium at 30° C. Cell numbers ($OD_{600}$) were adjusted and 5-fold serial dilutions were spotted on YPD or YPG agar plates.

Isolation of Mitochondria from Yeast

Yeast cells were grown at 24° C. (if not indicated otherwise) to an $OD_{600}$ of 1.0-1.5. Cells were harvested, washed in $dH_2O$ and incubated in DTT buffer (0.1 M $Tris/H_2SO_4$, pH 9.4, 10 mM DTT) for 20 min. After re-isolation cell pellets were resuspended in zymolyase buffer (1.2 M sorbitol, 20 mM $K_2HPO_4$/HCl, pH 7.4) supplemented with 3 mg/mg (wet weight cells) zymolyase and incubated for 40 min at 24° C. Resulting spheroblasts were washed in zymolyase buffer without enzyme and resuspended in homogenizing buffer (0.6 M sorbitol, 10 mM Tris/HCl, pH 7.4, 1 mM EDTA, 0.2% (w/v) BSA, 1 mM PMSF). Cells were subjected to 20 strokes in a glass homogenizer. Cellular debris was removed by two consecutive centrifugation steps for 5 min at 1500×g at 4° C. Mitochondria were isolated by centrifugation for 15 min at 16,000×g at 4° C. Mitochondria were suspended in SEM buffer (250 mM sucrose, 1 mM EDTA, 10 mM MOPS/KOH, pH 7.2) and protein concentration was determined by Bradford assay and adjusted to 10 mg/ml. Aliquots were snap-frozen in liquid nitrogen and stored at −80° C.

Processing and Degradation Assays Using Yeast Soluble Mitochondrial Extracts

Isolated mitochondria from yeast strains grown under respiratory conditions were washed with SEM buffer, re-isolated and resuspended in reaction buffer (250 mM sucrose, 10 mM MOPS/KOH, pH 7.2, 80 mM KCl, 5 mM $MgCl_2$, 5 mM $KH_2PO_4$) to a concentration of 3 µg/µl. Mitochondria were subjected to sonication (five times 30 s with 30 s breaks on ice, Sonifier250, Branson) followed by centrifugation at 100,000×g for 45 min at 4° C. The obtained supernatant was used for processing and degradation experiments. 0.5 µl of radiolabelled precursor protein and/or various peptides in different concentrations were added to 9 µl of yeast soluble mitochondrial extracts. Reactions were stopped by addition of 4× Laemmli buffer (8% (w/v) SDS, 0.08% (w/v) bromophenol blue, 40% (v/v) glycerol, 240 mM Tris/HCl, pH 6.8) containing 5% (v/v) β-mercaptoethanol and analyzed by SDS-PAGE followed by autoradiography and immunodecoration. Radiolabelled precursor proteins were synthesized with the transcription/translation rabbit reticulate lysate system (Promega) in the presence of $^{35}$S-methionine. Chemical amounts of Cym1 and control protein (Oct1) were synthesized in vitro using the RTS wheat germ system (5 PRIME). 0.5 µl of cell-free translation product was used in the processing assays.

Membrane Potential Measurement

The membrane potential (Δψ) was measured by fluorescence quenching. Isolated yeast mitochondria (50 µg) were incubated in 3 ml potential buffer (0.6 M sorbitol, 0.1% (w/v) BSA, 10 mM $MgCl_2$, 0.5 mM EDTA, 20 mM KPi, pH7.2) in the presence of 3 µl DiSC3 (3,3'-dipropylthiadicarbocyanine iodide, 2 mM in ethanol). Samples were mixed and absorption measured until a distribution equilibrium was reached (excitation 622 nm, emission 670 nm) using the luminescence spectrometer Aminco Bowman2 (Thermo Electron Corporation). The membrane potential was dissipated by addition of 4 µl valinomycin (1 mM in ethanol). Data were analysed with FL WinLab (Perkin Elmer).

High Resolution Respirometry

Mitochondrial respiration was measured with the Oxygraph 2-k (Oroboros Instruments, Austria) and analyzed with the DATLAB software. Measurements were performed at 30° C. in a 2 ml chamber. Isolated yeast mitochondria (100 µg) were added to 2 ml respiration buffer (10 mM MOPS/KOH, pH 7.2, 250 mM sucrose, 5 mM $MgCl_2$, 80 mM KCl, 5 mM $KP_i$) supplemented with 1 mM NADH and 1 mM ADP to obtain a basic respiration rate. The respiration rate was measured over a time-course of 5 min and the obtained wild-type values set to 100%.

Detection of Reactive Oxygen Species

For dihydroethidium (DHE) staining (10) 20 µg yeast mitochondria were washed with SEM buffer and incubated with 1 µM DHE in reaction buffer in the dark for 10 min. Fluorescence units were measured using a fluorescence reader (Infinite M200, Tecan) at an excitation wavelength of 480 nm and emission wavelength of 604 nm. Samples were measured in triplicates and background signals (samples without mitochondria) were subtracted. The wild-type values were set to 100%.

Expression and Purification of Mitochondrial Processing Peptidase (MPP) Complex

E. coli BL21 cells were transformed with plasmid pVG18 (32) that enables the transcription of a single mRNA encoding both β- (with N-terminal poly-histidine tag) and α-MPP subunits (Mas1 and Mas2) from S. cerevisiae. Cell cultures were grown in LB medium (10 g/l tryptone, 5 g/l yeast extract, 10 g/l NaCl) containing 100 µg/ml ampicillin at 37° C. to an $OD_{600}$ of 0.6. Expression was induced by addition of 1 mM IPTG (Isopropyl β-D-1-thiogalactopyranoside, Formedium) for 4 h. Cells were harvested and snap-frozen in liquid nitrogen. Pellets were resuspended in binding buffer (20 mM $Na_3PO_4$, 200 mM NaCl, 20 mM imidazole, pH 7.4) containing 1 mg/ml lysozyme (Sigma) and 10 µg/ml DNaseI (Sigma) and incubated for 1 h at 4° C. for cell lysis. The cell extract was centrifuged at 4000×g to remove unbroken cells. The supernatant was further centrifuged at 100,000×g for 30 min at 4° C. The obtained supernatant was incubated with Ni-NTA resin (Qiagen) for 3 h at 4° C. The resin was washed four times with binding buffer. Bound proteins were eluted with Elution buffer (20 mM Na3PO4, 200 mM NaCl, 200 mM imidazole, pH 7.4). The eluate was concentrated in a 50 kDa cut-off filter (Milipore) and applied to a Superdex 200 10/300 GL size-exclusion column equilibrated in 10 mM HEPES/KOH, pH 7.4, 50 mM NaCl, 1 mM DTT for further purification of the expressed protein.

MPP Activity Assays

Purified yeast MPP (0.15 µg protein) was incubated in processing buffer (10 mM HEPES/KOH, pH 7.4, 0.1 mM $MnCl_2$, 1 mM DTT, 0.1 mg/ml BSA) for 15 min at 30° C. (reaction volume of 20 µl) with the indicated peptides (see Miscellaneous). After pre-incubation, 1 µl of [$^{35}$S]-labeled $F_1β$ precursor protein (Nicotiana plumbaginifolia) was added and incubated for 10 min at 30° C. The reactions were stopped by addition of SDS-sample buffer (150 mM Tris/HCl, pH 7.0, 12% (w/v) SDS, 6% (w/v)β-mercaptoethanol, 30% (v/v) glycerol, 0.05% (w/v) bromophenol blue). The samples were analyzed by SDS-PAGE followed by autoradiography. Bands were quantified using the Multi Gauge software (Fuji Film). Experiments were performed in triplicates.

Transgenic Mice

The transgenic mouse line PS2APP (line B6.152H) is homozygous for both human PS2 N141I and APP Swedish FAD transgenes. (10, 27). As control wild-type age-matched C57Bl/6 mice were used. Mice were kept under an alternating cycle of 12-h light/12-h dark (lights were switched on at 6:00 am) at 20-22° C. Water and food was provided ad libitum. Strict adherence to the German federal regulations on animal protection and to the rules of the Association for Assessment and Accreditation of Laboratory Animal Care was maintained for an procedures and an experiments were carried out with the explicit approval of the local veterinary authority.

Isolation of Mitochondria from Mouse Tissue

One year old mice were sacrificed and brains aseptically removed from the skull. Brain stem and cerebellum were excised. An following steps were carried out on ice. Tissue was sliced with a scalpel and weighed. Samples were suspended in solution B (20 mM HEPES/KOH, pH 7.6, 220 mM mannitol, 70 mM sucrose, 1 mM EDTA, 0.5 mM PMSF) at approximately 10 ml/g brain tissue and homogenized by 30 strokes in a glass potter. Non-broken cells were removed by centrifugation at 800×g for 15 min at 4° C. Supernatant was subjected to centrifugation at 7000×g for 15 min at 4° C. for isolation of mitochondria. The mitochondrial pellet was resuspended in solution B and the protein concentration determined by Bradford protein assay. Samples were adjusted to 10 mg/ml with sucrose buffer (10 mM HEPES/KOH, pH 7.6, 0.5 M sucrose), aliquoted, snap-frozen in liquid nitrogen and stored at −80° C.

Processing Assays Using Mouse Soluble Mitochondrial Extracts

Isolated mitochondria were washed, re-isolated and solubilized in reaction buffer containing 1% (w/v) digitonin and 1 mM $MnCl_2$. Samples were incubated on ice for 15 min. After centrifugation at 20,000×g for 10 min at 4° C. the obtained supernatant was used for processing assays. Samples containing 60 μg mitochondrial extract in reaction buffer were incubated with 0.5 μl radiolabelled precursor protein at 37° C. for different times. The reactions were stopped by addition of 4× Laemmli buffer containing 5% (v/v) β-mercaptoethanol. Samples were analysed by SDS-PAGE followed by autoradiography and immunodecoration.

Organelle Isolation from Temporal Cortex of Human Brains

The tissue samples (temporal cortex from human brains) used in this study originated from individuals diagnosed with Alzheimer's disease (AD) and age-matched control individuals without AD and were obtained from the Karolinska Institute, Stockholm (table S2). Samples were collected according to local regulations for diagnostic purposes. The tissue samples were anonymized after diagnostic evaluation and used for this study with approval of the Ethical Committee (Dnr 2011/962-31/1, Stockholm). The temporal cortex regions were homogenized with a glass/Teflon homogenizer (15 strokes) in Buffer A (230 mM Mannitol, 70 mM Sucrose, 20 mM HEPES/KOH, pH 7.2, 0.5 mM EDTA). Unbroken cells and nuclei were removed by centrifugation at 484×g for 5 min at 4° C. In order to collect mitochondria the supernatant fraction was centrifuged at 7741×g for 10 min at 4° C. Both centrifugation steps were repeated. The mitochondrial pellet was resuspended in buffer A and the protein concentration determined by Bradford assay.

Expression of Aβ in Yeast

The plasmid encoding a cytosolically expressed TEV (Tobacco Etch Virus) protease (p416$^{TEVcyt}$) was generated by deleting the $b_2$-presequence of pRS416GAL1-$b_2$-TEV (33) by PCR using primers 5'-CGTCAAGGA-GAAAAAACCCCGGATTCTAGCATGAGATCCAGCTT-GTTTA AGGGACCACGTG-3' (SEQ ID No.: 1) and 5'-CACGTGGTCCCTTAAACAAGCTGGATCTCAT-GCTA GAATCCGGGGTTTTTTCTCCTTGACG-3' (SEQ ID No.: 2). For generation of the pESC$^{eGFP-Aβ}$ vector, eGFP was amplified by PCR, using pUG35(Ura) as template, with the primers 5'-ATCTGAATTCATGTCTAAAGGT-GAAGAATTATTCAC-3' (SEQ ID No.: 3) and 5'-ATCT-GAATTCTT TGTACAATTCATCCATACCATG-3' (SEQ ID No.: 4), digested with EcoRI and ligated into pESC(His) (Stratagene). This pESC-eGFP vector contained a linker (sequence: RIQPSLKGGRTS; according to the main part of the multiple cloning site (MCS)) to guarantee proper folding of eGFP and Aβ$^{1-42}$ and a stop codon in frame with the MCS. The cloning vector pESC-eGFP_G omitting the stop codon was created by PCR using primers 5'-ATCTGAATTCAT-GTCTAAAGGTGAAGAATTATTCAC-3' (SEQ ID No.: 5) and 5'-ATCTG AATTCGTTTGTACAATTCATCCATAC-CATG-3' (SEQ ID No.: 6). Aβ$^{1-42}$ was amplified by PCR with primers 5'-ATCTACTAGTATGGATGCAGAATTC-CGACATGAC-3' (Seq ID No.: 7) and 5'-ATCTATCG ATT-TACGCTATGACAACACCGCCC-3' (SEQ ID No.: 8) using pAS1N-Aβ-GFP as template (34), digested with SpeI and ClaI and cloned into pESC-eGFP_G. A TEV cleavage site was inserted 5' to Aβ$^{1-42}$ by PCR using primers 5'-GGGCGGCCGCACTAGTGAGAACCTGTACTTCCA-GTCCGATGCAGAATTCC GACATGACTCAGG-3' (SEQ ID No.: 9) and 5'-CGGAATTCTGCATCGGACTGGAAG-TACAGGTTCTCACTAGTGCGGCCGCC CTTTAGT-GAGGG-3' (SEQ ID No.: 10).

Strains were transformed with p416$^{Tevcyt}$ and pESC$^{eGFP-Aβ}$ or pESC$^{ev}$ (empty vector) as described above. Cells were grown in selective medium (6.7% (w/v) yeast nitrogen base without amino acids, 2% (w/v) glucose and 0.77% (w/v) Complete Supplement Mixture lacking histidine and uracil) at 30° C. For induction of expression, cells were shifted to selective medium containing 2% (w/v) galactose instead of glucose and incubated at 30° C. for 1 or 3 days, respectively. Yeast cell extracts were generated by the post-alkaline extraction method (35). Briefly, 2.5 $OD_{600}$ of yeast cells were washed with $dH_2O$, resuspended in 0.1 M NaOH and incubated for 5 minutes at 25° C. with 1400 rpm shaking. After re-isolation, cells were resuspended in 1× Laemmli buffer containing 5% (v/v) β-mercaptoethanol and analyzed by SDS-PAGE and immunodecoration.

Enrichment of N-Terminal Peptides Using COFRADIC

N-terminal COFRADIC was conducted as previously described with the following modifications (21, 36, 37). Highly pure mitochondria pellets (from yeast strains grown on YPG, 30° C.) were lysed in 500 μl of 2 M guanidium hydrochloride, 50 mM sodium phosphate, pH 8.7. Disulfide bonds were reduced by addition of 10 mM dithiotreithol for 30 min in 56° C. and free sulfhydryl groups were subsequently carbamidomethylated using 20 mM iodoacetamide at 25° C. in the dark. Afterwards, lysine residues were acetylated by incubation with 25 mM deutero-acetyl N-hydroxy-succimide for 1 h at 37° C. The reaction was quenched by adding a 4-fold molar excess of hydroxylamine and a 2-fold excess of glycine. Samples were diluted 10-fold with 50 mM ammonium bicarbonate, 5% (v/v) acetonitrile (ACN), 1 mM $CaCl_2$, pH 7.8 and digested with trypsin at 37° C. overnight (protease to protein ratio of 1:20). Generated peptides were purified by solid phase extraction with C18AR columns (Varian) according to the manufacturer's protocol and dried under vacuum. Peptides were reconstituted in 0.08% (v/v) trifluoroacetic acid (TFA), 50% (v/v) ACN, pH 2.7, and loaded onto a strong cation exchange (SCX) tip which was equilibrated with 10 mM $Na_3PO_4$, 50% (v/v) ACN, pH 2.7. Singly charged peptides were eluted with 10 mM $Na_3PO_4$, 50% (v/v) ACN, pH 2.7. This fraction was dried under vacuum and reconstituted in 100 μl of 10 mM ammonium acetate, 2% (v/v) ACN, pH 5.5. $H_2O_2$ was added to a final concentration of 0.5% (v/v) and incubated at 30° C. for 30 min, immediately prior to the primary RP-HPLC separation. Peptides were separated on an Ultimate 3000 LC system (Thermo Scientific) equipped with an 8-port valve WPS-T 3000 well plate sampler using a Zorbax 300SB-C18 column (5 μm particle size, 2.1×150 mm, Agilent) at a flow rate of 80 μl/min at 30° C. Solvent A was 10 mM ammonium acetate, 2% (v/v) ACN, pH 5.5, and solvent B was 10 mM ammonium acetate, 70% (v/v) ACN, pH 5.5. During the primary run 16 fractions of 4 min each were collected and subsequently dried under vacuum. Finally, peptides were reconstituted in 50 mM sodium borate, pH 9.5. For derivatization of free internal peptide N-termini 6 μM 2,4,6-trinitrobenzenesulfonic acid (TNBS) was added to each fraction and incubated for 30 min at 37° C. This step was repeated thrice. The reaction was stopped by addition of TFA to a final pH of 2. Afterwards, derivatized fractions were applied to a secondary RP-HPLC run, using identical chromatographic conditions as above. This time, fractions were recollected in a time frame starting 4 min before and ending 4 min after the original elution time in the primary run. Fractions were dried under vacuum and prepared for LC-MS analysis by reconstitution in 0.1% (v/v) TFA.

Nano-LC-MS/MS

Samples were analyzed on an LTQ-Orbitrap Velos mass spectrometer (Thermo Scientific), online coupled to a U3000 nano-HPLC system (Thermo Scientific). Peptides were preconcentrated on an in-house packed 100 μm inner diameter C18 trapping column (Synergi HydroRP, Phenomenex, 4 μm particle size, 80 Å pore size, 2 cm length) in 0.1% trifluoroacetic acid and separated on an in-house packed 75 μm inner diameter C18 main-column (Synergi HydroRP, Phenomenex, 2 μm particle size, 80 Å pore size, 30 cm length) applying a binary gradient from 4-42% acetonitrile in 0.1% formic acid. Dedicated wash blanks were introduced between consecutive samples to eliminate memory effects (38). MS survey scans were acquired in the Orbitrap from m/z 300 to 2000 at a resolution of 60,000 using the polysiloxane m/z 445.120030 as lock mass. The ten most intense signals were subjected to collision induced dissociation (CID) in the ion trap, taking into account a dynamic exclusion of 30 s. CID spectra were acquired with a normalized CE of 35%, an isolation width of 2 m/z, an activation time of 30 ms and a maximum injection time of 100 ms. Automatic gain control (AGC) target values were set to $10^6$ for MS and $10^4$ for MS/MS scans. Data interpretation was accomplished as previously described in (21).

Miscellaneous

Rabbits were immunized with synthetic peptides for generation of antibodies. The peptides were coupled to keyhole limpet hemocyanin (KLH) via a N- or C-terminal cysteine residue. The following peptide sequences were used: humanMDH2$^{preseq}$ MLSALARPASAALRRSFST-Cys (SEQ ID No.: 11), corresponding to presequence amino acids 1-19; yeastSod2$^{preseq}$ MFAKTAAANLTKKGED-Cys (SEQ ID No.: 12), corresponding to presequence amino acids 1-16; yeastCox4$^{preseq}$ MLSLRQSIRFFKPATRT-Cys (SEQ ID No.: 13), corresponding to presequence amino acids 1-17 and humanVDAC3 Cys-GKNFSAGGHKVGL-GFELEA (SEQ ID No.: 14).

Mouse and human proteins analysed by immunodecoration were probed with the following primary antibodies: anti-Amyloid-β (The Genetics Company, WO-02), anti-Cytochrome c (BD Pharmingen), mtHSP70 (anti-GRP75, Abcam, ab2799), SDHA (Abcam, ab14715).

SDS-PAGE and Immunodecoration was performed according to standard protocols and developed using ECL™ Western Blotting Detection Reagents (GE Healthcare) and X-ray films or the LAS 4000 system (Fujifilm). Non-relevant lanes were excised by digital processing.

Cox4$^{preseq}$ (MLSLRQSIRFFKPATRTLCSSRYLL) (SEQ ID No.: 15), Sdh1$^{octa}$ (FTSSALVR; EZ Biolab) (SEQ ID No.: 16) and Aβ$^{1-28}$ (DAEFRHDSGYEVHHQKLVFFAED-VGSNK; Anaspec) (SEQ ID No.: 17) peptides were dissolved in $dH_2O$ to a stock concentration of 1 mM and stored at −20° C. Aβ$^{1-40}$ peptides (DAEFRHDSGYEVHHQKLVF-FAEDVGSNKGAIIGLMVGGVV; Sigma, A1075) (SEQ ID No.: 18) were dissolved in $dH_2O$ to a stock concentration of 500 μM, sonicated (two times 10 s with 10 s breaks) and stored at −80° C. Aβ$^{scrambl.}$ peptides (KVKGLIDG-DHIGDLVYEFMDSNSAIFREGVGAGHVHVAQVEF) (SEQ ID No.: 19) were dissolved in 0.1% (w/v) $NH_4OH$ to a stock concentration of 1 mM and stored at −20° C. For in vitro processing assays the stocks were further diluted in reaction buffer.

TABLE S1

Yeast strains used in this study.

| # | Name | Genotype | Reference |
|---|------|----------|-----------|
| 1501 | Wild-type | MATa; ade2-101; his3-Δ200; leu2-Δ1; ura3-52; trp1-Δ63; lys2-801 | (40) |
| 3372 | cym1Δ | MATa; ade2-101; his3-Δ200; leu2-Δ1; ura3-52; trp1-Δ63; lys2-801; YDR430c::TRP1 | This study |
| 3675 | oct1Δ | MATa; ade2-101; his3-Δ200; leu2-Δ1; ura3-52; trp1-Δ63; lys2-801; YKL134c::HIS3MX6 | This study |
| 3676 | oct1Δcym1Δ | MATa; ade2-101; his3-Δ200; leu2-Δ1; ura3-52; trp1-Δ63; lys2-801; YDR430c::TRP1; YKL134c::HIS3MX6 | This study |
| 2263 | mas1 | Matα; ura3-52; trp1-1; leu2-3; leu2-112; his3-11; his3-15 | (41) |
| 3508 | mas1cym1Δ | Matα; ura3-52; trp1-1; leu2-3; leu2-112; his3-11; his3-15; YDR430c::HIS3MX6 | This study |

TABLE S1-continued

Yeast strains used in this study.

| # | Name | Genotype | Reference |
|---|---|---|---|
| 2876 | Cym1$^{H84Y}$ | MATα; can1Δ100; his3Δ11, 15; leu2Δ3, 112; ura3Δ1; ade2Δ1; trp1Δ1; YDR430c::KanMX6; YCplac111-CYM1(H84Y) | (26) |
| 2874 | Cym1$^{H88Y}$ | MATα; can1Δ100; his3Δ11, 15; leu2Δ3, 112; ura3Δ1; ade2Δ1; trp1Δ1; YDR430c::KanMX6; YCplac111-CYM1(H88Y) | (26) |
| 2873 | Cym1$^{E87Q}$ | MATα; can1Δ100; his3Δ11, 15; leu2Δ3, 112; ura3Δ1; ade2Δ1; trp1Δ1; YDR430c::KanMX6; YCplac111-CYM1(E87Q) | (26) |
| 2875 | Cym1 | MATα; can1Δ100; his3Δ11, 15; leu2Δ3, 112; ura3Δ1; ade2Δ1; trp1Δ1; YDR430c::KanMX6; YCplac111-CYM1(WT) | (26) |
| 3941 | coa6Δ | MATa; ade2-101; his3-Δ200; leu2-Δ1; ura3-52; trp1-Δ63; lys2-801; YMR244c-a::KanMX6 | This study |

TABLE S2

Overview of the human brain samples used in this study:

| Sample | Registration# | Age (y) | Sex | Post mortem (h) |
|---|---|---|---|---|
| C1 | 184 | 91 | Female | 12 |
| C2 | 190 | 86 | Female | 14 |
| C3 | 178 | 79 | Female | 5 |
| C4 | 188 | 64 | Female | 5 |
| AD1 | 216 | 80 | Female | 12 |
| AD2 | 253 | 70 | Female | 12 |
| AD3 | 215 | 72 | Female | 8 |
| AD4 | 255 | 78 | Female | 12 |

REFERENCES

1. J. Hardy, D. J. Selkoe, The amyloid hypothesis of Alzheimer's disease: progress and problems on the road to therapeutics. *Science* 297, 353-356 (2002).
2. V. A. Morais, B. de Strooper, Mitochondria dysfunction and neurodegenerative disorders: cause or consequence. *J. Alzheimers Dis.* 20, 255-263(2010).
3. S. Treusch et al., Functional links between Aβ toxicity, endocytic trafficking, and Alzheimer's disease risk factors in yeast. *Science* 334, 1241-1245 (2011).
4. E. Area-Gomez et al., Upregulated function of mitochondria-associated ER membranes in Alzheimer disease. *EMBO J.* 31, 4106-4123 (2012).
5. J. W. Lustbader et al., ABAD directly links Abeta to mitochondrial toxicity in Alzheimer's disease. *Science* 304, 448-452 (2004).
6. M. Manczak et al., Mitochondria are a direct site of Aβ accumulation in Alzheimer's disease neurons: implications for free radical generation and oxidative damage in disease progression. *Hum. Mol. Genet.* 15, 1437-1449 (2006).
7. H. Du et al., Cyclophilin D deficiency attenuates mitochondrial and neuronal perturbation and ameliorates learning and memory in Alzheimer's disease. *Nat. Med.* 14, 1097-1105 (2008).
8. P. J. Crouch et al., Mechanisms of Aβ mediated neurodegeneration in Alzheimer's disease. *Int. J. Biochem. Cell Biol.* 40, 181-198 (2008).
9. C. A. Hansson Petersen et al., The amyloid β-peptide is imported into mitochondria via the TOM import machinery and localized to mitochondrial cristae. *Proc. Natl. Acad. Sci. USA.* 105, 13145-13150 (2008).
10. V. Rhein et al., Amyloid-β and tau synergistically impair the oxidative phosphorylation system in triple transgenic Alzheimer's disease mice. *Proc. Natl. Acad. Sci. USA* 106, 20057-20062 (2009).
11. J. Yao et al., Mitochondrial bioenergetic deficit precedes Alzheimer's pathology in female mouse model of Alzheimer's disease. *Proc. Natl. Acad. Sci. USA* 106, 14670-14675 (2009).
12. L. M. Ittner, J. Götz, Amyloid-β and tau—a toxic pas de deux in Alzheimer's disease. *Nat. Rev. Neurosci.* 12, 65-72 (2011).
13. K. C. Walls et al., Swedish Alzheimer mutation induces mitochondrial dysfunction mediated by HSP60 mislocalization of amyloid precursor protein (APP) and beta-amyloid. *J. Biol. Chem.* 287, 30317-30327 (2012).
14. J. E. Selfridge, L. E., J. Lu, R. H. Swerdlow, Role of mitochondrial homeostasis and dynamics in Alzheimer's disease. *Neurobiol. Dis.* 51, 3-12 (2013).
15. A. Stahl et al., Isolation and identification of a novel mitochondrial metalloprotease (PreP) that degrades targeting presequences in plants. *J. Biol. Chem.* 277, 41931-41939 (2002).
16. A. Falkevall et al., Degradation of the amyloid β-protein by the novel mitochondrial peptidasome, PreP. *J. Biol. Chem.* 281, 29096-29104 (2006).
17. N. Alikhani et al., Decreased proteolytic activity of the mitochondrial amyloid-β degrading enzyme, PreP peptidasome, in Alzheimer's disease brain mitochondria. *J. Alzheimers Dis.* 27, 75-87 (2011).
18. G. Hawlitschek et al., Mitochondrial protein import: identification of processing peptidase and of PEP, a processing enhancing protein. *Cell* 53, 795-806 (1988).
19. M. J. Yang et al., The MAS-encoded processing protease of yeast mitochondria. Interaction of the purified enzyme with signal peptides and a purified precursor protein. *J. Biol. Chem.* 266, 6416-6423 (1991).
20. P. Dolezal, V. Likic, J. Tachezy, T. Lithgow, Evolution of the molecular machines for protein import into mitochondria. *Science* 313, 314-318 (2006).
21. F.-N. Vögtle et al., Global analysis of the mitochondrial N-proteome identifies a processing peptidase critical for protein stability. *Cell* 139, 428-439 (2009).

22. A. Mukhopadhyay, C.-S. Yang, B. Wei, H. Weiner, Precursor protein is readily degraded in mitochondrial matrix space if the leader is not processed by mitochondrial processing peptidase. *J. Biol. Chem.* 282, 37266-37275 (2007).
23. F.-N. Vögtle et al., Mitochondrial protein turnover: role of the precursor intermediate peptidase Oct1 in protein stabilization. *Mol. Biol. Cell* 22, 2135-2143 (2011).
24. A. Varshavsky, The N-end rule pathway and regulation by proteolysis. *Protein Sci.* 20, 1298-1345 (2011).
25. D. F. Tardiff et al., Yeast reveal a "druggable" RspS/Nedd4 network that ameliorates α-synuclein toxicity in neurons. *Science* 342, 979-983 (2013).
26. M. Kambacheld, S. Augustin, T. Tatsuta, S. Müner, T. Langer, Role of the novel metallopeptidase MoP112 and Saccharolysin for the complete degradation of proteins residing in different subcompartments of mitochondria. *J. Biol. Chem.* 280, 20132-20139 (2005).
27. L. Ozmen, A. Albientz, C. Czech, H. Jacobsen, Expression of transgenic APP mRNA is the key determinant for beta-amyloid deposition in PS2APP transgenic mice. *Neurodegener. Dis.* 6, 29-36 (2009).
28. F.-N. Vögtle et al., Intermembrane space proteome of yeast mitochondria. *Mol. Cell Proteomics* 11, 1840-1852 (2012).
29. N. G. Larsson, Somatic mitochondrial DNA mutations in mammalian aging. *Ann. Rev. Biochem.* 79, 683-706 (2010).
30. I. Begcevic et al., Semiquantitative proteomics analysis of human hippocampal tissues from Alzheimer's disease and age-matched control brains. *Clinical Proteomics* 10, 5 (2013).
31. R. S. Sikorski, P. Hieter P. A system of shuttle vectors and yeast host strains designed for efficient manipulation of DNA in *Saccharomyces cerevisiae*. *Genetics* 122, 19-27 (1989).
32. C. Witte, R. E. Jensen, M. P. Yaffe, G. Schatz, MAS1, a gene essential for yeast mitochondrial assembly, encodes a subunit of the mitochondrial processing protease. *EMBO J.* 7, 1439-1447 (1988).
33. M. Longtine et al., Additional modules for versatile and economical PCR-based gene deletion and modification in *Saccharomyces cerevisiae*. *Yeast* 14, 953-961 (1998).
34. V. Géli, Functional reconstitution in *Escherichia coli* of the yeast mitochondrial matrix peptidase from its two inactive subunits. *Proc. Natl. Acad. Sci. USA.* 90, 6247-6251 (1993).
35. N. Kondo-Okamoto, J. M. Shaw, K. Okamoto, Mmm1p spans both the outer and inner mitochondrial membranes and contains distinct domains for targeting and foci formation. *J. Biol. Chem.* 278, 48997-49005 (2003).
36. J. Caine et al., Alzheimer's Abeta fused to green fluorescent protein induces growth stress and a heat shock response. *FEMS Yeast Res.* 7, 1230-1236 (2007).
37. V. V. Kushnirov, Rapid and reliable protein extraction from yeast. *Yeast* 16, 857-860 (2000).
38. K. Gevaert et al., Exploring proteomes and analyzing protein processing by mass spectrometric identification of sorted N-terminal peptides. *Nat. Biotechnol.* 21, 566-569 (2003).
39. A. Staes et al., Selecting protein N-terminal peptides by combined fractional diagonal chromatography. *Nat. Protoc.* 6, 1130-1141 (2011).
40. J. M. Burkhart, T. Premsler, A. Sickmann, Quality control of nano-LC-MS systems using stable isotope-coded peptides. *Proteomics* 11, 1049-1057 (2011).
41. D. Stojanovski, N. Pfanner, N. Wiedemann, Import of proteins into mitochondria. *Meth. Cell Biol.* 80, 783-806 (2007).
42. uniprot.org
43. Alam, I., et al. (2012). "Flow cytometric lymphocyte subset analysis using material from frozen whole blood." Journal of immunoassay & immunochemistry 33(2): 128-139.

The invention claimed is:

1. A method of detecting an amount of at least one premature mitochondrial protein in a sample, the method comprising the following steps:
   a) providing a sample from a patient potentially suffering from Alzheimer's disease (AD); and
   b) detecting an amount of at least one premature mitochondrial protein in said sample, wherein said premature mitochondrial protein comprises at least part of its mitochondrium-targeting presequence, wherein the amount of said at least one premature mitochondrial protein is determined by a mass-spectrometry method, wherein said mass-spectrometry method selectively detects the at least one premature mitochondrial protein comprising at least part of its mitochondrium targeting presequence via the at least part of its mitochondrium-targeting presequence.

2. The method according to claim 1, wherein said sample is a blood sample or a brain sample.

3. The method according to claim 1, wherein said at least one premature mitochondrial protein is the protein mitochondrial human malate dehydrogenase 2 (hMdh2).

* * * * *

```
                        SEQUENCE LISTING

<160> NUMBER OF SEQ ID NOS: 80

<210> SEQ ID NO 1
<211> LENGTH: 61
<212> TYPE: DNA
<213> ORGANISM: Artificial Sequence
<220> FEATURE:
<223> OTHER INFORMATION: Artificially synthesized oligonucleotide primer

<400> SEQUENCE: 1
cgtcaaggag aaaaaacccc ggattctagc atgagatcca gcttgtttaa gggaccacgt    60
g                                                                    61

<210> SEQ ID NO 2
<211> LENGTH: 61
<212> TYPE: DNA
<213> ORGANISM: Artificial Sequence
<220> FEATURE:
<223> OTHER INFORMATION: Artificially synthesized oligonucleotide primer

<400> SEQUENCE: 2
cacgtggtcc cttaaacaag ctggatctca tgctagaatc cggggttttt tctccttgac    60
g                                                                    61

<210> SEQ ID NO 3
```

```
<211> LENGTH: 36
<212> TYPE: DNA
<213> ORGANISM: Artificial Sequence
<220> FEATURE:
<223> OTHER INFORMATION: Artificially synthesized oligonucleotide primer

<400> SEQUENCE: 3
atctgaattc atgtctaaag gtgaagaatt attcac                              36

<210> SEQ ID NO 4
<211> LENGTH: 34
<212> TYPE: DNA
<213> ORGANISM: Artificial Sequence
<220> FEATURE:
<223> OTHER INFORMATION: Artificially synthesized oligonucleotide primer

<400> SEQUENCE: 4
atctgaattc tttgtacaat tcatccatac catg                                34

<210> SEQ ID NO 5
<211> LENGTH: 36
<212> TYPE: DNA
<213> ORGANISM: Artificial Sequence
<220> FEATURE:
<223> OTHER INFORMATION: Artificially synthesized oligonucleotide primer

<400> SEQUENCE: 5
atctgaattc atgtctaaag gtgaagaatt attcac                              36

<210> SEQ ID NO 6
<211> LENGTH: 35
<212> TYPE: DNA
<213> ORGANISM: Artificial Sequence
<220> FEATURE:
<223> OTHER INFORMATION: Artificially synthesized oligonucleotide primer

<400> SEQUENCE: 6
atctgaattc gtttgtacaa ttcatccata ccatg                               35

<210> SEQ ID NO 7
<211> LENGTH: 34
<212> TYPE: DNA
<213> ORGANISM: Artificial Sequence
<220> FEATURE:
<223> OTHER INFORMATION: Artificially synthesized oligonucleotide primer

<400> SEQUENCE: 7
atctactagt atggatgcag aattccgaca tgac                                34

<210> SEQ ID NO 8
<211> LENGTH: 32
<212> TYPE: DNA
<213> ORGANISM: Artificial Sequence
<220> FEATURE:
<223> OTHER INFORMATION: Artificially synthesized oligonucleotide primer

<400> SEQUENCE: 8
atctatcgat ttacgctatg acaacaccgc cc                                  32

<210> SEQ ID NO 9
<211> LENGTH: 63
<212> TYPE: DNA
<213> ORGANISM: Artificial Sequence
<220> FEATURE:
<223> OTHER INFORMATION: Artificially synthesized oligonucleotide primer

<400> SEQUENCE: 9
```

```
gggcggccgc actagtgaga acctgtactt ccagtccgat gcagaattcc gacatgactc    60
agg                                                                  63

<210> SEQ ID NO 10
<211> LENGTH: 62
<212> TYPE: DNA
<213> ORGANISM: Artificial Sequence
<220> FEATURE:
<223> OTHER INFORMATION: Artificially synthesized oligonucleotide primer

<400> SEQUENCE: 10
cggaattctg catcggactg gaagtacagg ttctcactag tgcggccgcc ctttagtgag    60
gg                                                                   62

<210> SEQ ID NO 11
<211> LENGTH: 20
<212> TYPE: PRT
<213> ORGANISM: Artificial Sequence
<220> FEATURE:
<223> OTHER INFORMATION: Artificially synthesized peptide

<400> SEQUENCE: 11

Met Leu Ser Ala Leu Ala Arg Pro Ala Ser Ala Ala Leu Arg Arg Ser
1               5                   10                  15

Phe Ser Thr Cys
            20

<210> SEQ ID NO 12
<211> LENGTH: 17
<212> TYPE: PRT
<213> ORGANISM: Artificial Sequence
<220> FEATURE:
<223> OTHER INFORMATION: Artificially synthesized peptide

<400> SEQUENCE: 12

Met Phe Ala Lys Thr Ala Ala Ala Asn Leu Thr Lys Lys Gly Glu Asp
1               5                   10                  15

Cys

<210> SEQ ID NO 13
<211> LENGTH: 18
<212> TYPE: PRT
<213> ORGANISM: Artificial Sequence
<220> FEATURE:
<223> OTHER INFORMATION: Artificially synthesized peptide

<400> SEQUENCE: 13

Met Leu Ser Leu Arg Gln Ser Ile Arg Phe Phe Lys Pro Ala Thr Arg
1               5                   10                  15

Thr Cys

<210> SEQ ID NO 14
<211> LENGTH: 20
<212> TYPE: PRT
<213> ORGANISM: Artificial Sequence
<220> FEATURE:
<223> OTHER INFORMATION: Artificially synthesized peptide

<400> SEQUENCE: 14

Cys Gly Lys Asn Phe Ser Ala Gly Gly His Lys Val Gly Leu Gly Phe
1               5                   10                  15

Glu Leu Glu Ala
```

```
                         20

<210> SEQ ID NO 15
<211> LENGTH: 25
<212> TYPE: PRT
<213> ORGANISM: Artificial Sequence
<220> FEATURE:
<223> OTHER INFORMATION: Artificially synthesized peptide

<400> SEQUENCE: 15

Met Leu Ser Leu Arg Gln Ser Ile Arg Phe Phe Lys Pro Ala Thr Arg
1               5                   10                  15

Thr Leu Cys Ser Ser Arg Tyr Leu Leu
            20                  25

<210> SEQ ID NO 16
<211> LENGTH: 8
<212> TYPE: PRT
<213> ORGANISM: Artificial Sequence
<220> FEATURE:
<223> OTHER INFORMATION: Artificially synthesized peptide

<400> SEQUENCE: 16

Phe Thr Ser Ser Ala Leu Val Arg
1               5

<210> SEQ ID NO 17
<211> LENGTH: 28
<212> TYPE: PRT
<213> ORGANISM: Artificial Sequence
<220> FEATURE:
<223> OTHER INFORMATION: Artificially synthesized peptide

<400> SEQUENCE: 17

Asp Ala Glu Phe Arg His Asp Ser Gly Tyr Glu Val His His Gln Lys
1               5                   10                  15

Leu Val Phe Phe Ala Glu Asp Val Gly Ser Asn Lys
            20                  25

<210> SEQ ID NO 18
<211> LENGTH: 40
<212> TYPE: PRT
<213> ORGANISM: Artificial Sequence
<220> FEATURE:
<223> OTHER INFORMATION: Artificially synthesized peptide

<400> SEQUENCE: 18

Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
            20                  25                  30

Gly Leu Met Val Gly Gly Val Val
        35                  40

<210> SEQ ID NO 19
<211> LENGTH: 42
<212> TYPE: PRT
<213> ORGANISM: Artificial Sequence
<220> FEATURE:
<223> OTHER INFORMATION: Artificially synthesized peptide

<400> SEQUENCE: 19

Lys Val Lys Gly Leu Ile Asp Gly Asp His Ile Gly Asp Leu Val Tyr
1               5                   10                  15
```

Glu Phe Met Asp Ser Asn Ser Ala Ile Phe Arg Glu Gly Val Gly Ala
                 20                  25                  30

Gly His Val His Val Ala Gln Val Glu Phe
        35                  40

<210> SEQ ID NO 20
<211> LENGTH: 24
<212> TYPE: PRT
<213> ORGANISM: Artificial Sequence
<220> FEATURE:
<223> OTHER INFORMATION: Artificially synthesized presequence peptide

<400> SEQUENCE: 20

Met Leu Ser Ala Leu Ala Arg Pro Ala Ser Ala Ala Leu Arg Arg Ser
1               5                   10                  15

Phe Ser Thr Ser Ala Gln Asn Asn
            20

<210> SEQ ID NO 21
<211> LENGTH: 35
<212> TYPE: PRT
<213> ORGANISM: artificial
<220> FEATURE:
<223> OTHER INFORMATION: Artificially synthesized presequence peptide

<400> SEQUENCE: 21

Met Phe Ser Lys Leu Ala His Leu Gln Arg Phe Ala Val Leu Ser Arg
1               5                   10                  15

Gly Val His Ser Ser Val Ala Ser Ala Thr Ser Val Ala Thr Lys Lys
                20                  25                  30

Thr Val Gln
        35

<210> SEQ ID NO 22
<211> LENGTH: 40
<212> TYPE: PRT
<213> ORGANISM: artificial
<220> FEATURE:
<223> OTHER INFORMATION: Artificially synthesized presequence peptide

<400> SEQUENCE: 22

Met Gln Ala Ala Arg Met Ala Ala Ser Leu Gly Arg Gln Leu Leu Arg
1               5                   10                  15

Leu Gly Gly Gly Ser Ser Arg Leu Thr Ala Leu Leu Gly Gln Pro Arg
                20                  25                  30

Pro Gly Pro Ala Arg Arg Pro Tyr
            35                  40

<210> SEQ ID NO 23
<211> LENGTH: 33
<212> TYPE: PRT
<213> ORGANISM: artificial
<220> FEATURE:
<223> OTHER INFORMATION: Artificially synthesized presequence peptide

<400> SEQUENCE: 23

Met Ala Ala Val Val Leu Ala Ala Thr Arg Leu Leu Arg Gly Ser Gly
1               5                   10                  15

Ser Trp Gly Cys Ser Arg Leu Arg Phe Gly Pro Pro Ala Tyr Arg Arg
                20                  25                  30

Phe

-continued

```
<210> SEQ ID NO 24
<211> LENGTH: 22
<212> TYPE: PRT
<213> ORGANISM: artificial
<220> FEATURE:
<223> OTHER INFORMATION: Artificially synthesized presequence peptide

<400> SEQUENCE: 24

Met Ala Leu Arg Leu Leu Arg Arg Ala Ala Arg Gly Ala Ala Ala Ala
1               5                   10                  15

Ala Leu Leu Arg Leu Lys
            20

<210> SEQ ID NO 25
<211> LENGTH: 29
<212> TYPE: PRT
<213> ORGANISM: artificial
<220> FEATURE:
<223> OTHER INFORMATION: Artificially synthesized presequence peptide

<400> SEQUENCE: 25

Met Ser Thr Ala Ala Leu Ile Thr Leu Val Arg Ser Gly Gly Asn Gln
1               5                   10                  15

Val Arg Arg Arg Val Leu Leu Ser Ser Arg Leu Leu Gln
            20                  25

<210> SEQ ID NO 26
<211> LENGTH: 28
<212> TYPE: PRT
<213> ORGANISM: artificial
<220> FEATURE:
<223> OTHER INFORMATION: Artificially synthesized presequence peptide

<400> SEQUENCE: 26

Met Ala Ala Ser Ala Ala Arg Gly Ala Ala Ala Leu Arg Arg Ser Ile
1               5                   10                  15

Asn Gln Pro Val Ala Phe Val Arg Arg Ile Pro Trp
            20                  25

<210> SEQ ID NO 27
<211> LENGTH: 23
<212> TYPE: PRT
<213> ORGANISM: artificial
<220> FEATURE:
<223> OTHER INFORMATION: Artificially synthesized presequence peptide
      fragment

<400> SEQUENCE: 27

Met Leu Ser Ala Leu Ala Arg Pro Ala Ser Ala Ala Leu Arg Arg Ser
1               5                   10                  15

Phe Ser Thr Ser Ala Gln Asn
            20

<210> SEQ ID NO 28
<211> LENGTH: 22
<212> TYPE: PRT
<213> ORGANISM: artificial
<220> FEATURE:
<223> OTHER INFORMATION: Artificially synthesized presequence peptide
      fragment

<400> SEQUENCE: 28

Met Leu Ser Ala Leu Ala Arg Pro Ala Ser Ala Ala Leu Arg Arg Ser
1               5                   10                  15

Phe Ser Thr Ser Ala Gln
            20
```

-continued

```
            20

<210> SEQ ID NO 29
<211> LENGTH: 21
<212> TYPE: PRT
<213> ORGANISM: artificial
<220> FEATURE:
<223> OTHER INFORMATION: Artificially synthesized presequence peptide
      fragment

<400> SEQUENCE: 29

Met Leu Ser Ala Leu Ala Arg Pro Ala Ser Ala Ala Leu Arg Arg Ser
1               5                   10                  15

Phe Ser Thr Ser Ala
            20

<210> SEQ ID NO 30
<211> LENGTH: 20
<212> TYPE: PRT
<213> ORGANISM: artificial
<220> FEATURE:
<223> OTHER INFORMATION: Artificially synthesized presequence peptide
      fragment

<400> SEQUENCE: 30

Met Leu Ser Ala Leu Ala Arg Pro Ala Ser Ala Ala Leu Arg Arg Ser
1               5                   10                  15

Phe Ser Thr Ser
            20

<210> SEQ ID NO 31
<211> LENGTH: 19
<212> TYPE: PRT
<213> ORGANISM: artificial
<220> FEATURE:
<223> OTHER INFORMATION: Artificially synthesized presequence peptide
      fragment

<400> SEQUENCE: 31

Met Leu Ser Ala Leu Ala Arg Pro Ala Ser Ala Ala Leu Arg Arg Ser
1               5                   10                  15

Phe Ser Thr

<210> SEQ ID NO 32
<211> LENGTH: 18
<212> TYPE: PRT
<213> ORGANISM: artificial
<220> FEATURE:
<223> OTHER INFORMATION: Artificially synthesized presequence peptide
      fragment

<400> SEQUENCE: 32

Met Leu Ser Ala Leu Ala Arg Pro Ala Ser Ala Ala Leu Arg Arg Ser
1               5                   10                  15

Phe Ser

<210> SEQ ID NO 33
<211> LENGTH: 17
<212> TYPE: PRT
<213> ORGANISM: Artificial Sequence
<220> FEATURE:
<223> OTHER INFORMATION: Artificially synthesized presequence peptide
      fragment

<400> SEQUENCE: 33
```

```
Met Leu Ser Ala Leu Ala Arg Pro Ala Ser Ala Ala Leu Arg Arg Ser
1               5                   10                  15
Phe

<210> SEQ ID NO 34
<211> LENGTH: 16
<212> TYPE: PRT
<213> ORGANISM: Artificial Sequence
<220> FEATURE:
<223> OTHER INFORMATION: Artificially synthesized presequence peptide
      fragment

<400> SEQUENCE: 34

Met Leu Ser Ala Leu Ala Arg Pro Ala Ser Ala Ala Leu Arg Arg Ser
1               5                   10                  15

<210> SEQ ID NO 35
<211> LENGTH: 15
<212> TYPE: PRT
<213> ORGANISM: Artificial Sequence
<220> FEATURE:
<223> OTHER INFORMATION: Artificially synthesized presequence peptide
      fragment

<400> SEQUENCE: 35

Met Leu Ser Ala Leu Ala Arg Pro Ala Ser Ala Ala Leu Arg Arg
1               5                   10                  15

<210> SEQ ID NO 36
<211> LENGTH: 14
<212> TYPE: PRT
<213> ORGANISM: Artificial Sequence
<220> FEATURE:
<223> OTHER INFORMATION: Artificially synthesized presequence peptide
      fragment

<400> SEQUENCE: 36

Met Leu Ser Ala Leu Ala Arg Pro Ala Ser Ala Ala Leu Arg
1               5                   10

<210> SEQ ID NO 37
<211> LENGTH: 13
<212> TYPE: PRT
<213> ORGANISM: Artificial Sequence
<220> FEATURE:
<223> OTHER INFORMATION: Artificially synthesized presequence peptide
      fragment

<400> SEQUENCE: 37

Met Leu Ser Ala Leu Ala Arg Pro Ala Ser Ala Ala Leu
1               5                   10

<210> SEQ ID NO 38
<211> LENGTH: 12
<212> TYPE: PRT
<213> ORGANISM: Artificial Sequence
<220> FEATURE:
<223> OTHER INFORMATION: Artificially synthesized presequence peptide
      fragment

<400> SEQUENCE: 38

Met Leu Ser Ala Leu Ala Arg Pro Ala Ser Ala Ala
1               5                   10

<210> SEQ ID NO 39
<211> LENGTH: 34
<212> TYPE: PRT
```

<213> ORGANISM: Artificial Sequence
<220> FEATURE:
<223> OTHER INFORMATION: Artificially synthesized presequence peptide
      fragment

<400> SEQUENCE: 39

Met Phe Ser Lys Leu Ala His Leu Gln Arg Phe Ala Val Leu Ser Arg
1               5                   10                  15

Gly Val His Ser Ser Val Ala Ser Ala Thr Ser Val Ala Thr Lys Lys
            20                  25                  30

Thr Val

<210> SEQ ID NO 40
<211> LENGTH: 31
<212> TYPE: PRT
<213> ORGANISM: Artificial Sequence
<220> FEATURE:
<223> OTHER INFORMATION: Artificially synthesized presequence peptide
      fragment

<400> SEQUENCE: 40

Met Phe Ser Lys Leu Ala His Leu Gln Arg Phe Ala Val Leu Ser Arg
1               5                   10                  15

Gly Val His Ser Ser Val Ala Ser Ala Thr Ser Val Ala Thr Lys
            20                  25                  30

<210> SEQ ID NO 41
<211> LENGTH: 28
<212> TYPE: PRT
<213> ORGANISM: Artificial Sequence
<220> FEATURE:
<223> OTHER INFORMATION: Artificially synthesized presequence peptide
      fragment

<400> SEQUENCE: 41

Met Phe Ser Lys Leu Ala His Leu Gln Arg Phe Ala Val Leu Ser Arg
1               5                   10                  15

Gly Val His Ser Ser Val Ala Ser Ala Thr Ser Val
            20                  25

<210> SEQ ID NO 42
<211> LENGTH: 23
<212> TYPE: PRT
<213> ORGANISM: Artificial Sequence
<220> FEATURE:
<223> OTHER INFORMATION: Artificially synthesized presequence peptide
      fragment

<400> SEQUENCE: 42

Met Phe Ser Lys Leu Ala His Leu Gln Arg Phe Ala Val Leu Ser Arg
1               5                   10                  15

Gly Val His Ser Ser Val Ala
            20

<210> SEQ ID NO 43
<211> LENGTH: 16
<212> TYPE: PRT
<213> ORGANISM: Artificial Sequence
<220> FEATURE:
<223> OTHER INFORMATION: Artificially synthesized presequence peptide
      fragment

<400> SEQUENCE: 43

Met Phe Ser Lys Leu Ala His Leu Gln Arg Phe Ala Val Leu Ser Arg
1               5                   10                  15

<210> SEQ ID NO 44
<211> LENGTH: 34
<212> TYPE: PRT
<213> ORGANISM: Artificial Sequence
<220> FEATURE:
<223> OTHER INFORMATION: Artificially synthesized presequence peptide fragment

<400> SEQUENCE: 44

```
Met Gln Ala Ala Arg Met Ala Ala Ser Leu Gly Arg Gln Leu Leu Arg
1               5                   10                  15

Leu Gly Gly Gly Ser Ser Arg Leu Thr Ala Leu Leu Gly Gln Pro Arg
            20                  25                  30

Pro Gly
```

<210> SEQ ID NO 45
<211> LENGTH: 31
<212> TYPE: PRT
<213> ORGANISM: Artificial Sequence
<220> FEATURE:
<223> OTHER INFORMATION: Artificially synthesized presequence peptide fragment

<400> SEQUENCE: 45

```
Met Gln Ala Ala Arg Met Ala Ala Ser Leu Gly Arg Gln Leu Leu Arg
1               5                   10                  15

Leu Gly Gly Gly Ser Ser Arg Leu Thr Ala Leu Leu Gly Gln Pro
            20                  25                  30
```

<210> SEQ ID NO 46
<211> LENGTH: 28
<212> TYPE: PRT
<213> ORGANISM: Artificial Sequence
<220> FEATURE:
<223> OTHER INFORMATION: Artificially synthesized presequence peptide fragment

<400> SEQUENCE: 46

```
Met Gln Ala Ala Arg Met Ala Ala Ser Leu Gly Arg Gln Leu Leu Arg
1               5                   10                  15

Leu Gly Gly Gly Ser Ser Arg Leu Thr Ala Leu Leu
            20                  25
```

<210> SEQ ID NO 47
<211> LENGTH: 23
<212> TYPE: PRT
<213> ORGANISM: Artificial Sequence
<220> FEATURE:
<223> OTHER INFORMATION: Artificially synthesized presequence peptide fragment

<400> SEQUENCE: 47

```
Met Gln Ala Ala Arg Met Ala Ala Ser Leu Gly Arg Gln Leu Leu Arg
1               5                   10                  15

Leu Gly Gly Gly Ser Ser Arg
            20
```

<210> SEQ ID NO 48
<211> LENGTH: 14
<212> TYPE: PRT
<213> ORGANISM: Artificial Sequence
<220> FEATURE:
<223> OTHER INFORMATION: Artificially synthesized presequence peptide fragment

<400> SEQUENCE: 48

Met Gln Ala Ala Arg Met Ala Ala Ser Leu Gly Arg Gln Leu
1               5                   10

<210> SEQ ID NO 49
<211> LENGTH: 27
<212> TYPE: PRT
<213> ORGANISM: Artificial Sequence
<220> FEATURE:
<223> OTHER INFORMATION: Artificially synthesized presequence peptide
      fragment

<400> SEQUENCE: 49

Met Ala Ala Val Val Leu Ala Ala Thr Arg Leu Leu Arg Gly Ser Gly
1               5                   10                  15

Ser Trp Gly Cys Ser Arg Leu Arg Phe Gly Pro
            20                  25

<210> SEQ ID NO 50
<211> LENGTH: 26
<212> TYPE: PRT
<213> ORGANISM: Artificial Sequence
<220> FEATURE:
<223> OTHER INFORMATION: Artificially synthesized presequence peptide
      fragment

<400> SEQUENCE: 50

Met Ala Ala Val Val Leu Ala Ala Thr Arg Leu Leu Arg Gly Ser Gly
1               5                   10                  15

Ser Trp Gly Cys Ser Arg Leu Arg Phe Gly
            20                  25

<210> SEQ ID NO 51
<211> LENGTH: 25
<212> TYPE: PRT
<213> ORGANISM: Artificial Sequence
<220> FEATURE:
<223> OTHER INFORMATION: Artificially synthesized presequence peptide
      fragment

<400> SEQUENCE: 51

Met Ala Ala Val Val Leu Ala Ala Thr Arg Leu Leu Arg Gly Ser Gly
1               5                   10                  15

Ser Trp Gly Cys Ser Arg Leu Arg Phe
            20                  25

<210> SEQ ID NO 52
<211> LENGTH: 24
<212> TYPE: PRT
<213> ORGANISM: Artificial Sequence
<220> FEATURE:
<223> OTHER INFORMATION: Artificially synthesized presequence peptide
      fragment

<400> SEQUENCE: 52

Met Ala Ala Val Val Leu Ala Ala Thr Arg Leu Leu Arg Gly Ser Gly
1               5                   10                  15

Ser Trp Gly Cys Ser Arg Leu Arg
            20

<210> SEQ ID NO 53
<211> LENGTH: 23
<212> TYPE: PRT
<213> ORGANISM: Artificial Sequence

```
<220> FEATURE:
<223> OTHER INFORMATION: Artificially synthesized presequence peptide
      fragment

<400> SEQUENCE: 53

Met Ala Ala Val Val Leu Ala Ala Thr Arg Leu Leu Arg Gly Ser Gly
1               5                   10                  15

Ser Trp Gly Cys Ser Arg Leu
            20

<210> SEQ ID NO 54
<211> LENGTH: 21
<212> TYPE: PRT
<213> ORGANISM: Artificial Sequence
<220> FEATURE:
<223> OTHER INFORMATION: Artificially synthesized presequence peptide
      fragment

<400> SEQUENCE: 54

Met Ala Leu Arg Leu Leu Arg Arg Ala Ala Arg Gly Ala Ala Ala Ala
1               5                   10                  15

Ala Leu Leu Arg Leu
            20

<210> SEQ ID NO 55
<211> LENGTH: 20
<212> TYPE: PRT
<213> ORGANISM: Artificial Sequence
<220> FEATURE:
<223> OTHER INFORMATION: Artificially synthesized presequence peptide
      fragment

<400> SEQUENCE: 55

Met Ala Leu Arg Leu Leu Arg Arg Ala Ala Arg Gly Ala Ala Ala Ala
1               5                   10                  15

Ala Leu Leu Arg
            20

<210> SEQ ID NO 56
<211> LENGTH: 19
<212> TYPE: PRT
<213> ORGANISM: Artificial Sequence
<220> FEATURE:
<223> OTHER INFORMATION: Artificially synthesized presequence peptide
      fragment+

<400> SEQUENCE: 56

Met Ala Leu Arg Leu Leu Arg Arg Ala Ala Arg Gly Ala Ala Ala Ala
1               5                   10                  15

Ala Leu Leu

<210> SEQ ID NO 57
<211> LENGTH: 18
<212> TYPE: PRT
<213> ORGANISM: Artificial Sequence
<220> FEATURE:
<223> OTHER INFORMATION: Artificially synthesized presequence peptide
      fragment

<400> SEQUENCE: 57

Met Ala Leu Arg Leu Leu Arg Arg Ala Ala Arg Gly Ala Ala Ala Ala
1               5                   10                  15

Ala Leu
```

```
<210> SEQ ID NO 58
<211> LENGTH: 17
<212> TYPE: PRT
<213> ORGANISM: Artificial Sequence
<220> FEATURE:
<223> OTHER INFORMATION: Artificially synthesized presequence peptide
      fragment

<400> SEQUENCE: 58

Met Ala Leu Arg Leu Leu Arg Arg Ala Ala Arg Gly Ala Ala Ala Ala
1               5                   10                  15

Ala

<210> SEQ ID NO 59
<211> LENGTH: 26
<212> TYPE: PRT
<213> ORGANISM: Artificial Sequence
<220> FEATURE:
<223> OTHER INFORMATION: Artificially synthesized presequence peptide
      fragment

<400> SEQUENCE: 59

Met Ser Thr Ala Ala Leu Ile Thr Leu Val Arg Ser Gly Gly Asn Gln
1               5                   10                  15

Val Arg Arg Arg Val Leu Leu Ser Ser Arg
            20                  25

<210> SEQ ID NO 60
<211> LENGTH: 24
<212> TYPE: PRT
<213> ORGANISM: Artificial Sequence
<220> FEATURE:
<223> OTHER INFORMATION: Artificially synthesized presequence peptide
      fragment

<400> SEQUENCE: 60

Met Ser Thr Ala Ala Leu Ile Thr Leu Val Arg Ser Gly Gly Asn Gln
1               5                   10                  15

Val Arg Arg Arg Val Leu Leu Ser
            20

<210> SEQ ID NO 61
<211> LENGTH: 22
<212> TYPE: PRT
<213> ORGANISM: Artificial Sequence
<220> FEATURE:
<223> OTHER INFORMATION: Artificially synthesized presequence peptide
      fragment

<400> SEQUENCE: 61

Met Ser Thr Ala Ala Leu Ile Thr Leu Val Arg Ser Gly Gly Asn Gln
1               5                   10                  15

Val Arg Arg Arg Val Leu
            20

<210> SEQ ID NO 62
<211> LENGTH: 20
<212> TYPE: PRT
<213> ORGANISM: Artificial Sequence
<220> FEATURE:
<223> OTHER INFORMATION: Artificially synthesized presequence peptide
      fragment

<400> SEQUENCE: 62

Met Ser Thr Ala Ala Leu Ile Thr Leu Val Arg Ser Gly Gly Asn Gln
1               5                   10                  15
```

Val Arg Arg Arg
        20

<210> SEQ ID NO 63
<211> LENGTH: 19
<212> TYPE: PRT
<213> ORGANISM: Artificial Sequence
<220> FEATURE:
<223> OTHER INFORMATION: Artificially synthesized presequence peptide
      fragment

<400> SEQUENCE: 63

Met Ser Thr Ala Ala Leu Ile Thr Leu Val Arg Ser Gly Gly Asn Gln
1               5                   10                  15

Val Arg Arg

<210> SEQ ID NO 64
<211> LENGTH: 23
<212> TYPE: PRT
<213> ORGANISM: Artificial Sequence
<220> FEATURE:
<223> OTHER INFORMATION: Artificially synthesized presequence peptide
      fragment

<400> SEQUENCE: 64

Met Ala Ala Ser Ala Ala Arg Gly Ala Ala Ala Leu Arg Arg Ser Ile
1               5                   10                  15

Asn Gln Pro Val Ala Phe Val
        20

<210> SEQ ID NO 65
<211> LENGTH: 22
<212> TYPE: PRT
<213> ORGANISM: Artificial Sequence
<220> FEATURE:
<223> OTHER INFORMATION: Artificially synthesized presequence peptide
      fragment

<400> SEQUENCE: 65

Met Ala Ala Ser Ala Ala Arg Gly Ala Ala Ala Leu Arg Arg Ser Ile
1               5                   10                  15

Asn Gln Pro Val Ala Phe
        20

<210> SEQ ID NO 66
<211> LENGTH: 17
<212> TYPE: PRT
<213> ORGANISM: Artificial Sequence
<220> FEATURE:
<223> OTHER INFORMATION: Artificially synthesized presequence peptide
      fragment

<400> SEQUENCE: 66

Met Ala Ala Ser Ala Ala Arg Gly Ala Ala Ala Leu Arg Arg Ser Ile
1               5                   10                  15

Asn

<210> SEQ ID NO 67
<211> LENGTH: 16
<212> TYPE: PRT
<213> ORGANISM: Artificial Sequence
<220> FEATURE:
<223> OTHER INFORMATION: Artificially synthesized presequence peptide
      fragment

```
<400> SEQUENCE: 67

Met Ala Ala Ser Ala Ala Arg Gly Ala Ala Ala Leu Arg Arg Ser Ile
1               5                   10                  15

<210> SEQ ID NO 68
<211> LENGTH: 14
<212> TYPE: PRT
<213> ORGANISM: Artificial Sequence
<220> FEATURE:
<223> OTHER INFORMATION: Artificially synthesized presequence peptide
      fragment

<400> SEQUENCE: 68

Met Ala Ala Ser Ala Ala Arg Gly Ala Ala Ala Leu Arg Arg
1               5                   10

<210> SEQ ID NO 69
<211> LENGTH: 35
<212> TYPE: PRT
<213> ORGANISM: Artificial Sequence
<220> FEATURE:
<223> OTHER INFORMATION: Artificially synthesized presequence peptide

<400> SEQUENCE: 69

Met Ala Ala Ala Ala Gln Ser Arg Val Val Arg Val Leu Ser Met Ser
1               5                   10                  15

Arg Ser Ala Ile Thr Ala Ile Ala Thr Ser Val Cys His Gly Pro Pro
            20                  25                  30

Cys Arg Gln
        35

<210> SEQ ID NO 70
<211> LENGTH: 22
<212> TYPE: PRT
<213> ORGANISM: Artificial Sequence
<220> FEATURE:
<223> OTHER INFORMATION: Artificially synthesized presequence peptide

<400> SEQUENCE: 70

Met Ala Arg Asn Val Val Tyr Pro Leu Tyr Arg Leu Gly Gly Pro Gln
1               5                   10                  15

Leu Arg Val Phe Arg Thr
            20

<210> SEQ ID NO 71
<211> LENGTH: 29
<212> TYPE: PRT
<213> ORGANISM: Artificial Sequence
<220> FEATURE:
<223> OTHER INFORMATION: Artificially synthesized presequence peptide
      fragment

<400> SEQUENCE: 71

Met Ala Ala Ala Ala Gln Ser Arg Val Val Arg Val Leu Ser Met Ser
1               5                   10                  15

Arg Ser Ala Ile Thr Ala Ile Ala Thr Ser Val Cys His
            20                  25

<210> SEQ ID NO 72
<211> LENGTH: 24
<212> TYPE: PRT
<213> ORGANISM: Artificial Sequence
<220> FEATURE:
<223> OTHER INFORMATION: Artificially synthesized presequence peptide
      fragment
```

<400> SEQUENCE: 72

Met Ala Ala Ala Ala Gln Ser Arg Val Val Arg Val Leu Ser Met Ser
1               5                   10                  15

Arg Ser Ala Ile Thr Ala Ile Ala
            20

<210> SEQ ID NO 73
<211> LENGTH: 20
<212> TYPE: PRT
<213> ORGANISM: Artificial Sequence
<220> FEATURE:
<223> OTHER INFORMATION: Artificially synthesized presequence peptide
      fragment

<400> SEQUENCE: 73

Met Ala Ala Ala Ala Gln Ser Arg Val Val Arg Val Leu Ser Met Ser
1               5                   10                  15

Arg Ser Ala Ile
            20

<210> SEQ ID NO 74
<211> LENGTH: 18
<212> TYPE: PRT
<213> ORGANISM: Artificial Sequence
<220> FEATURE:
<223> OTHER INFORMATION: Artificially synthesized presequence peptide
      fragment

<400> SEQUENCE: 74

Met Ala Ala Ala Ala Gln Ser Arg Val Val Arg Val Leu Ser Met Ser
1               5                   10                  15

Arg Ser

<210> SEQ ID NO 75
<211> LENGTH: 16
<212> TYPE: PRT
<213> ORGANISM: Artificial Sequence
<220> FEATURE:
<223> OTHER INFORMATION: Artificially synthesized presequence peptide
      fragment

<400> SEQUENCE: 75

Met Ala Ala Ala Ala Gln Ser Arg Val Val Arg Val Leu Ser Met Ser
1               5                   10                  15

<210> SEQ ID NO 76
<211> LENGTH: 21
<212> TYPE: PRT
<213> ORGANISM: Artificial Sequence
<220> FEATURE:
<223> OTHER INFORMATION: Artificially synthesized presequence peptide
      fragment

<400> SEQUENCE: 76

Met Ala Arg Asn Val Val Tyr Pro Leu Tyr Arg Leu Gly Gly Pro Gln
1               5                   10                  15

Leu Arg Val Phe Arg
            20

<210> SEQ ID NO 77
<211> LENGTH: 20
<212> TYPE: PRT
<213> ORGANISM: Artificial Sequence
<220> FEATURE:

```
<223> OTHER INFORMATION: Artificially synthesized presequence peptide
      fragment

<400> SEQUENCE: 77

Met Ala Arg Asn Val Val Tyr Pro Leu Tyr Arg Leu Gly Gly Pro Gln
1               5                   10                  15

Leu Arg Val Phe
            20

<210> SEQ ID NO 78
<211> LENGTH: 19
<212> TYPE: PRT
<213> ORGANISM: Artificial Sequence
<220> FEATURE:
<223> OTHER INFORMATION: Artificially synthesized presequence peptide
      fragment

<400> SEQUENCE: 78

Met Ala Arg Asn Val Val Tyr Pro Leu Tyr Arg Leu Gly Gly Pro Gln
1               5                   10                  15

Leu Arg Val

<210> SEQ ID NO 79
<211> LENGTH: 18
<212> TYPE: PRT
<213> ORGANISM: Artificial Sequence
<220> FEATURE:
<223> OTHER INFORMATION: Artificially synthesized presequence peptide
      fragment

<400> SEQUENCE: 79

Met Ala Arg Asn Val Val Tyr Pro Leu Tyr Arg Leu Gly Gly Pro Gln
1               5                   10                  15

Leu Arg

<210> SEQ ID NO 80
<211> LENGTH: 17
<212> TYPE: PRT
<213> ORGANISM: Artificial Sequence
<220> FEATURE:
<223> OTHER INFORMATION: Artificially synthesized presequence peptide
      fragment

<400> SEQUENCE: 80

Met Ala Arg Asn Val Val Tyr Pro Leu Tyr Arg Leu Gly Gly Pro Gln
1               5                   10                  15

Leu
```